(12) United States Patent
Corbett et al.

(10) Patent No.: US 11,986,602 B2
(45) Date of Patent: May 21, 2024

(54) CATHETER OF A HEART PUMP SHAPED FOR ANATOMIC FIT

(71) Applicant: Abiomed, Inc., Danvers, MA (US)

(72) Inventors: Scott C. Corbett, Beverly, MA (US); Margaret Tierney Bergson, Georgetown, MA (US)

(73) Assignee: Abiomed, Inc., Danvers, MA (US)

( * ) Notice: Subject to any disclaimer, the term of this patent is extended or adjusted under 35 U.S.C. 154(b) by 595 days.

(21) Appl. No.: 15/168,852

(22) Filed: May 31, 2016

(65) Prior Publication Data
US 2017/0340787 A1 Nov. 30, 2017

(51) Int. Cl.
*A61M 25/00* (2006.01)
*A61M 60/13* (2021.01)
(Continued)

(52) U.S. Cl.
CPC ...... *A61M 25/002* (2013.01); *A61M 25/0009* (2013.01); *A61M 25/0041* (2013.01); *A61M 60/13* (2021.01); *A61M 60/216* (2021.01); *A61M 60/857* (2021.01); *A61M 2209/06* (2013.01)

(58) Field of Classification Search
CPC .... A61M 1/1008; A61M 1/125; A61M 1/101; A61M 25/002; A61M 25/0009; A61M 25/0041; A61M 2209/06
See application file for complete search history.

(56) References Cited

U.S. PATENT DOCUMENTS 3,839,841 A 10/1974 Amplatz
5,584,803 A * 12/1996 Stevens ................. A61M 25/10
604/6.16
(Continued)

FOREIGN PATENT DOCUMENTS

EP 2258302 A1 12/2010
JP 2001509416 A 7/2001
(Continued)

OTHER PUBLICATIONS

Daniel Giant et al. Imaging of Mechanical Cardiac Assist Devices Year: 2011, vol. 1, Issue: 1, May, https://doi.org/10.4103/2156-7514.80373DO.*

(Continued)

*Primary Examiner* — Nathan J Jenness
*Assistant Examiner* — James Moss
(74) *Attorney, Agent, or Firm* — Botos Churchill IP Law LLP

(57) ABSTRACT

A heart pump assembly, also referred to as catheter assembly, having a desired anatomical shape is provided. The catheter assembly can include a catheter and a cannula having a bend between a proximal portion and a distal portion. A resting shape of the catheter and the cannula can be selected to allow the distal cannula portion to be positioned at a desired angle relative to an anatomical plane (e.g., a plane of an aortic arch). In some embodiments, a packaging tray can be designed to set the catheter assembly in a desired resting shape. For example, the proximal cannula portion can be positioned at a first angle relative to the catheter, and the proximal cannula portion can be positioned at a second angle out of the plane of the packaging tray via one or more inserts.

10 Claims, 16 Drawing Sheets

(51) Int. Cl.
*A61M 60/216* (2021.01)
*A61M 60/857* (2021.01)

(56) References Cited

U.S. PATENT DOCUMENTS

| | | | | |
|---|---|---|---|---|
| 5,848,691 | A * | 12/1998 | Morris | A61M 25/002 206/364 |
| 5,873,842 | A * | 2/1999 | Brennen | A61M 25/0136 600/585 |
| 5,873,865 | A * | 2/1999 | Horzewski | A61M 25/0662 606/15 |
| 6,083,260 | A * | 7/2000 | Aboul-Hosn | A61M 1/3653 600/16 |
| 6,544,216 | B1 | 4/2003 | Sammler et al. | |
| 2005/0279370 | A1 * | 12/2005 | Aboul-Hosn | A61M 1/3653 604/9 |
| 2010/0268017 | A1 * | 10/2010 | Siess | A61M 1/101 600/16 |
| 2011/0127186 | A1 | 6/2011 | Enns et al. | |
| 2012/0158021 | A1 * | 6/2012 | Morrill | A61M 25/0136 606/139 |
| 2012/0203056 | A1 * | 8/2012 | Corbett | A61M 60/135 600/16 |
| 2014/0110296 | A1 | 4/2014 | Terzibashian | |
| 2015/0080743 | A1 * | 3/2015 | Siess | A61B 5/02154 600/478 |
| 2019/0046707 | A1 * | 2/2019 | Aboul-Hosn | A61M 60/857 |

FOREIGN PATENT DOCUMENTS

| | | | |
|---|---|---|---|
| JP | 2015514531 A | | 5/2015 |
| WO | 9902099 A2 | | 1/1999 |
| WO | 0731720 A1 | * | 10/2002 |
| WO | 2015057999 A1 | | 4/2015 |
| WO | 2015/175711 A1 | | 11/2015 |

OTHER PUBLICATIONS

Medgadget, https://www.medgadget.com/2015/03/abiomed-impella-2-5-heart-pump-fda-approved.html, Mar. 24, 2015.*

Engström, A. E. (2012). Percutaneous mechanical circulatory support for treatment and prevention of hemodynamic instability. https://pure.uva.nl/ws/files/1555394/108075_08.pdf.*

Inas Mohammad et al. . Building a bridge to save a failing ventricle: radiologic evaluation of short- and long-term cardiac assist devices. Radiographics 2015; 35:327-56, https://doi.org/10.1148/rg.352140149, Published Mar. 12, 2015.*

Tuseth V, et al. Percutaneous left ventricular assist device can prevent acute cerebral ischaemia during ventricular fibrillation. Resuscitation. Oct. 2009;80(10):1197-203. doi: 10.1016/j.resuscitation.2009.05.012. Epub Jul. 23, 2009. PMID: 19631443.viewed on Apr. 24, 2021.*

Impella Ventricular Support Systems for Use During Cardiogenic Shock Instructions for use and Clinical Reference manual, https://fda.report/PMA/P140003/14/P140003S005D.pdf, 2015.*

International Search Report PCT/US2017/035249, dated Dec. 12, 2017.

Office Action for corresponding Japanese Application No. 2018-562632 dated Jun. 2, 2021 (9 pages).

Office Action from corresponding Australian Patent Application No. 2017273561 dated Jan. 21, 2022 (6 pages).

Office Action from corresponding Israel Patent Application No. 263090 dated Nov. 25, 2021 8 pages.

Office Action from corresponding Israeli Patent Application No. 263090 dated Mar. 29, 2023 (8 pp.).

Office Action from corresponding Australian Patent Application No. 2022263596 dated Dec. 12, 2023 (3 pp.).

Office Action from corresponding Japanese Patent Application No. 2023110378 dated Apr. 2, 2024 (9 pp.).

* cited by examiner

US 11,986,602 B2

CATHETER OF A HEART PUMP SHAPED FOR ANATOMIC FIT

BACKGROUND

A mechanical circulatory support device, also commonly referred to as a heart pump assembly or catheter assembly, can be introduced in the heart and can be configured to assist or replace the natural cardiac pump function with cyclical or continuous pumping of blood. The heart pump assembly may include a pump, a cannula, and a catheter. When deployed in the left side of the heart, the heart pump assembly pulls blood from the left ventricle of the heart and expels blood into the aorta; when deployed in the right side of the heart the pump pulls blood from the inferior vena cava and expels it into the pulmonary artery. Heart pump assemblies are introduced surgically or percutaneously during a cardiac procedure. In one approach, pump assemblies intended for the left heart are inserted by a catheterization procedure through the femoral artery.

During a catheterization procedure which prepares for insertion of the pump into the left heart, an introducer is inserted into the femoral artery through an arteriotomy to gain access to the artery and create an insertion path. A placement guidewire can be advanced into the artery along the insertion path. After the guidewire has been inserted into the artery, the pump assembly can be advanced over the guidewire and into the patient. Alternatively, the pump assembly can be inserted directly into the artery without a guidewire. The pump can be inserted via a standard catheterization procedure through the femoral artery, into the ascending aorta, across the aortic valve and into the left ventricle. When deployed in the left heart, the pump assembly pulls blood from the left ventricle through an inlet area near the tip and expels blood from the cannula into the ascending aorta.

The pump assembly can be advanced over the guidewire or directly into the vessel, as described above, and advanced to a desired axial position relative to the heart. To position the pump assembly in a desired rotational orientation, a user can apply torque to the catheter, resulting in torsion/twisting of the catheter and rotation of a distal portion of the catheter and/or of the cannula.

Prior to being inserted into a patient, a catheter of the pump has an inherent shape and there is a limited amount of torque that can be safely applied to the catheter before the applied torque is released in an uncontrollable manner such that the catheter recoils. The inherent shape of the catheter (i.e. the resting or unstressed shape of the catheter, when no external forces are imposed thereon) can be affected during manufacturing and/or insertion. For example, sterilization is part of the manufacturing process and can include applying and removing heat and humidity in an alternating or cyclical fashion (referred to herein as thermocycling). Because the catheter is sensitive to thermocycling, once the thermocycling is complete, the catheter sets in a new resting shape. The above-mentioned resting shape after thermocycling can be determined by features of the pump itself and/or features that hold the catheter in a specific shape such as its packaging tray. However, the resulting resting shape of the catheter may not match the patient's anatomy. Because a limited amount of torque can be applied to the catheter, it can be difficult to position the cannula in a desired axial location and rotational orientation in a patient.

SUMMARY

Systems, methods, and devices are described herein for providing a catheter assembly of a heart pump having a shape that facilitates positioning of the pump assembly within a patient. The catheter assembly can include a catheter and a cannula coupled thereto. The plane of the cannula can be at an angular offset relative to the plane of the catheter. In some implementations, this angular offset is achieved by applying torsion to the catheter and setting the shape of the catheter using heat or other methods. In other implementations, the angular offset is achieved without applying torsion to the catheter. For example, this may be achieved by rotating the cannula relative to the catheter before coupling the catheter and cannula, preshaping a backbone of the catheter, and/or by rotating the catheter's connection to the handle and/or the cannula. In addition or alternative to changing the rotation angle between the catheter and the cannula, the cannula may be translated within the plane of the catheter and/or out of the plane of the catheter and then the shape can be set. Translation of the cannula in the plane of the catheter can be measured by a bend angle between the proximal portion of the cannula and an axis of a fixed proximal portion of the catheter. Translation of the cannula out of the plane of the catheter can be measured by the angular offset between the proximal portion of the cannula and a plane of the fixed proximal portion of the catheter.

Rotation and/or translation of the cannula shifts the inlet of the pump toward free space of a ventricle (e.g., the left ventricle). For example, this can facilitate navigation and positioning the pump assembly in the left ventricle and can reduce the occurrence of suction events and low blood flow alarms. The catheter can be shaped and the cannula can be oriented such that the cannula can be positioned in the left ventricle of the heart angled towards the apex of the ventricle and with the inlet of the pump located in the ventricle's free space, thereby reducing the occurrence of suctioning of the heart wall and/or biomaterial ingestion. The rotation angle of the cannula can result in a predetermined placement of the catheter and the cannula in a desired location. For example, the rotation angle can be selected to be about equal to an angle between a plane of the aortic arch and a predetermined cannula placement plane. In such a case, rotation of the cannula with respect to the catheter also biases a distal portion of the pump assembly away from chordae which actuate the mitral valve. This can reduce the chance of the pump assembly being caught therein which could make extracting the pump more difficult.

In implementations in which the rotation angle is achieved by torsioning/twisting the catheter, thermal treatment can set the shape of the catheter. This thermal treatment can occur during sterilization of the catheter during which temperature, pressure, and/or humidity can be cycled to set the shape of the catheter (e.g., by setting the shape of a metal or polymer spine of the catheter). This shape setting occurs as the material is relaxed and/or annealed at a high temperature and then set at a lower temperature. In one example, to form the catheter assembly in an anatomically correct position, the catheter spine is imparted with a rotation angle and/or translation during sterilization which biases the catheter in a desired orientation.

The resulting new, baseline unstressed shape of the catheter, formed by shaping a catheter spine during sterilization or by any of the other methods described herein, reduces the need to apply torque to the catheter during insertion and positioning of the pump assembly within the vessels of the patient (e.g., through the aorta and along the aortic arch). The improved catheter assembly may be helpful for the IMPELLA® 5.0 pump, IMPELLA® 2.5 pump, IMPELLA CP® pump assemblies which are adapted for use in the left ventricle, or may be helpful for any other heart pumps.

Furthermore, the relative position of the cannula and the catheter can be selected to best fit the anatomy of a particular patient or category of patients. This improved fit can also help reduce delivery time.

An unstressed catheter and a cannula rotated or translated away from a proximal portion of the catheter may be presented in a tray (e.g., a packaging tray). Alternatively, an unstressed catheter and a cannula rotated or translated away from a proximal portion of the catheter may be manufactured or presented without a tray. A tray may be configured to apply and maintain torsion in the catheter prior to thermocycling (e.g., sterilization) of the catheter assembly. For example, a first portion of the tray may immobilize a first location on the catheter and a second portion of the tray may immobilize a second location on the cannula such that the cannula is rotated and the distal portion of the cannula is at an angle relative to the plane of the tray, as described above. The tray may include a structure which allows the cannula to lie in a plane which is different from the plane of the catheter and the packaging tray. After the catheter assembly is thermally treated in the desired position, for example a position initially maintained by the two tray portions, the catheter retains its torsion/twisted shape in an unstressed, resting state, and the cannula retains its shape and angular position when the catheter assembly is removed from the tray and during insertion into a patient.

Also disclosed herein are methods of manufacturing a catheter assembly having the configurations described above. According to one method, the proximal catheter portion is held fixed, and the cannula is rotated and/or translated until the cannula is in the desired location relative to the catheter. The cannula is then held fixed and thermocycling is performed. After completion of the thermocycling process, the shape of the catheter is set. In this configuration the catheter is no longer under stress when in the set shape. In another method, the cannula, the catheter, or both are rotated relative to one another to achieve a particular desired angle between the distal portion of the cannula and a reference plane (e.g., the plane of the aortic arch). In some implementations, a handle coupled to the catheter assembly is rotated relative to the catheter assembly or one or more components of the catheter assembly and the shape of the assembly is set.

In one aspect, a catheter assembly includes a catheter including a proximal catheter portion, a longitudinal axis, a distal catheter portion, and a catheter transition portion between the proximal catheter portion and the distal catheter portion, wherein the longitudinal axis forms a curve. The catheter assembly further includes a cannula coupled to the distal catheter portion, the cannula having a proximal cannula portion, a distal cannula portion, and a cannula transition portion comprising a bend between the proximal cannula portion and the distal cannula portion. When the cannula is inserted in a heart, the distal cannula portion lies within a first plane, and the curve of the longitudinal axis of the catheter portion lies in a second plane, where the first plane is different from, and at an angular offset relative to the second plane.

In certain implementations, the angular offset of the first plane relative to the second plane is about substantially equal to an angle between a plane of an aortic arch defined by an ascending portion of an aorta and a descending portion of the aorta and a plane defined by the ascending portion of the aorta and an apex of a left ventricle of a heart.

In certain implementations, the angular offset is selected such that the catheter assembly has a predetermined anatomical shape when in the resting state.

In certain implementations, the angular offset biases the distal cannula portion toward the apex of the left ventricle of the heart when the catheter assembly is inserted through the aorta.

In certain implementations, the angular offset is between about 64° and 125°.

In certain implementations, the angular offset is about 92°.

In certain implementations, the angular offset is such that the distal catheter portion is pointed toward an apex of the heart.

In certain implementations, the catheter assembly further includes a stylet inserted into the catheter to adjust a shape of the distal catheter portion.

In certain implementations, the catheter assembly further includes a catheter handle connected to the proximal catheter portion and rotated to adjust a position of the distal catheter portion.

In certain implementations, the catheter assembly further includes a steering mechanism connected to the proximal catheter portion and configured to adjust a position of the distal catheter portion after insertion.

In another aspect, a catheter assembly includes a catheter including a proximal catheter portion, a distal catheter portion, and a catheter transition portion between the proximal catheter portion and the distal catheter portion. The catheter assembly further includes a cannula coupled to the distal catheter portion, the cannula having a proximal cannula portion, a distal cannula portion, and a cannula transition portion comprising a bend between the proximal cannula portion and the distal cannula portion. When the cannula is inserted in a heart of a patient, the distal cannula portion lies within a first plane that is different from, and at an angular offset relative to, a second plane in which an aortic arch of the patient lies.

In certain implementations, the angular offset is about substantially equal to or greater than an angle between a plane of an aortic arch defined by an ascending portion of an aorta and a descending portion of the aorta and a plane defined by defined by the ascending portion of the aorta and an apex of a left ventricle of the heart.

In certain implementations, the angular offset is selected such that the catheter assembly has a predetermined anatomical shape when in a resting state.

In certain implementations, the angular offset biases the distal cannula portion toward the apex of a left ventricle of a heart when the catheter assembly is inserted through the aorta of the patient.

In certain implementations, the angular offset is between about 64° and 125°.

In certain implementations, the angular offset is about 92°.

In certain implementations, the angular offset is such that the distal catheter portion is pointed toward an apex of the heart.

In certain implementations, the catheter assembly further includes a stylet inserted into the catheter to adjust a shape of the distal catheter portion.

In certain implementations, the catheter assembly further includes a catheter handle connected to the proximal catheter portion and rotated to adjust a position of the distal catheter portion.

In certain implementations, the catheter assembly further includes a steering mechanism connected to the proximal catheter portion and configured to adjust a position of the distal catheter portion after insertion.

In certain implementations, the catheter assembly further includes an inner polyamide layer and an outer polyurethane layer.

In yet another aspect, a method for setting a catheter assembly in a desired anatomical shape includes forming a longitudinal axis of a catheter into a curve which lies within a second plane. The catheter includes a proximal catheter portion, a longitudinal axis, a distal catheter portion, and a catheter transition portion between the proximal catheter portion and the distal catheter portion. The method further includes rotating a cannula relative to the catheter such that the first plane is at an angular offset relative to the second plane. The cannula includes a longitudinal axis, a proximal cannula portion, a distal cannula portion, and a bend between the proximal cannula portion and the distal cannula portion, wherein the distal cannula portion lies within a first plane. The method further includes connecting the proximal cannula portion to the distal catheter portion.

In certain implementations, the angular offset of the first plane relative to the second plane is about substantially equal to an angle between a plane of an aortic arch defined by an ascending portion of an aorta and a descending portion of the aorta and a plane defined by the ascending portion of the aorta and an apex of a left ventricle of a heart.

In certain implementations, the method further includes rotating the cannula relative to the catheter is before the connecting the proximal cannula portion to the distal catheter portion.

In certain implementations, the method further includes rotating the cannula relative to the catheter is after the connecting the proximal cannula portion to the distal catheter portion.

In certain implementations, the method further includes, before the rotating, engaging the catheter with a first insert, thereby preventing movement of the catheter relative to the second plane.

In certain implementations, the method further includes before the rotating, engaging the catheter with a second insert, thereby preventing movement of the distal cannula portion relative to the first plane.

In certain implementations, the method further includes, after the rotating, thermocycling the catheter assembly such that a resting shape of the catheter assembly is set after completion of the thermocycling.

In yet another aspect, a system for configuring a catheter assembly into an anatomical shape includes a catheter assembly including a catheter and a cannula coupled to the catheter, the cannula having a proximal cannula portion, a distal cannula portion, and a cannula transition portion comprising a bend between the proximal cannula portion and the distal cannula portion. The system further includes a packaging tray that houses the catheter assembly and includes a first insert and a second insert, the first insert being coupled to the cannula and the second insert being coupled to the catheter. Between the first insert and the second insert the catheter is torsioned by a torsion angle such that the distal cannula portion is rotated at a first angle out of a plane of the packaging tray.

In certain implementations, the first angle is about equal to an angle between a plane of an aortic arch and a predetermined cannula placement location.

In certain implementations, the first angle is between about 60° and 140°.

In certain implementations, the first angle biases the distal cannula portion away from a mitral valve of a heart when the catheter assembly is inserted through the aorta of a patient.

In certain implementations, the first angle is about equal to the angle between a plane of an aortic arch defined by an ascending portion of an aorta and a descending portion of the aorta and a plane defined by the ascending portion of the aorta and an apex of a left ventricle of a heart.

In certain implementations, the first angle is about 92°.

In yet another aspect, a method for setting a catheter assembly in a desired anatomical shape includes positioning a catheter assembly inside a packaging tray. The packaging tray houses the catheter assembly, and the catheter assembly includes a catheter and a cannula connected to the catheter, the cannula including a bend between a proximal cannula portion and a distal cannula portion. The method further includes engaging the catheter with a first insert, thereby preventing movement of the catheter relative to the packaging tray. The method further includes rotating the cannula by a rotation angle relative to the packaging tray and engaging the catheter with a second insert, thereby preventing movement of the cannula relative to the packaging tray. The method further includes thermocycling the catheter assembly such that a resting shape of the catheter assembly is set after completion of the thermocycling.

In certain implementations, the rotation angle is about equal to an angle between a plane of an aortic arch and a desired plane for the distal cannula portion, and the rotation angle is configured such that a plane of the distal cannula portion is at the angle between the plane of the aortic arch and the desired plane for the distal cannula portion.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
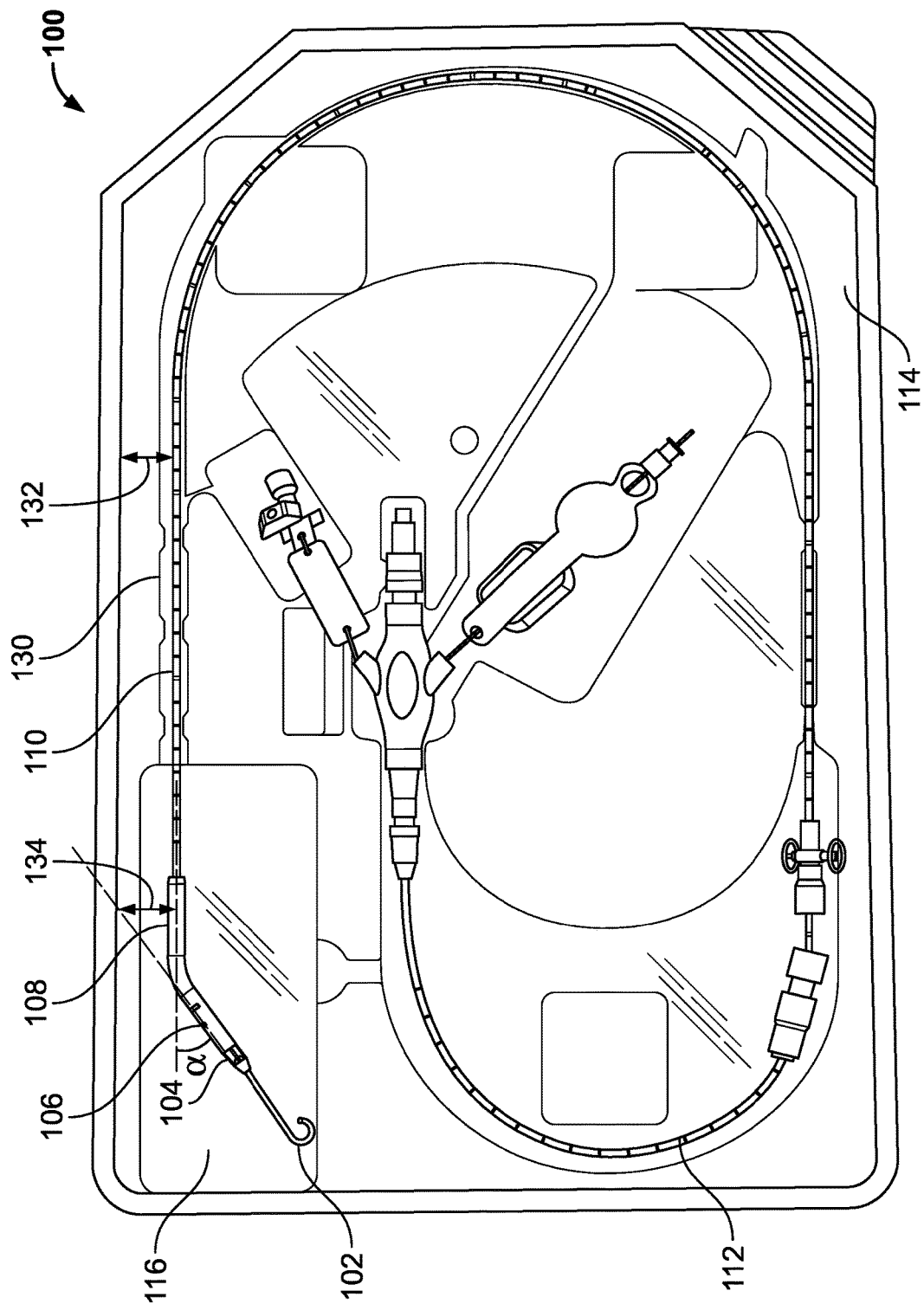
FIG. 1 shows an exemplary prior art pump assembly.

Systems, methods, and devices are described herein for providing a catheter assembly of a heart pump having a shape that facilitates positioning of the pump assembly within a patient. The catheter assembly can include a catheter and a cannula coupled thereto. The plane of the cannula can be at an angular offset relative to the plane of the catheter. In some implementations, this angular offset is achieved by applying torsion to the catheter and setting the shape of the catheter using heat or other methods. In other implementations, the angular offset is achieved without applying torsion to the catheter. For example, this may be achieved by rotating the cannula relative to the catheter before coupling the catheter and cannula, preshaping a backbone of the catheter, and/or by rotating the catheter's connection to the handle and/or the cannula. In addition or alternative to changing the rotation angle between the catheter and the cannula, the cannula may be translated within the plane of the catheter and/or out of the plane of the catheter and then the shape can be set. Translation of the cannula in the plane of the catheter can be measured by a bend angle between the proximal portion of the cannula and an axis of a fixed proximal portion of the catheter. Translation of the cannula out of the plane of the catheter can be measured by the angular offset between the proximal portion of the cannula and a plane of the fixed proximal portion of the catheter.

Rotation and/or translation of the cannula shifts the inlet of the pump toward free space of a ventricle (e.g., the left ventricle). For example, this can facilitate navigation and positioning the pump assembly in the left ventricle and can reduce the occurrence of suction events and low blood flow alarms. The catheter can be shaped and the cannula can be oriented such that the cannula can be positioned in the left ventricle of the heart angled towards the apex of the ventricle and with the inlet of the pump located in the ventricle's free space, thereby reducing the occurrence of suctioning of the heart wall and/or biomaterial ingestion. The rotation angle of the cannula can result in a predetermined placement of the catheter and the cannula in a desired location. For example, the rotation angle can be selected to be about equal to an angle between a plane of the aortic arch and a predetermined cannula placement plane. In such a case, rotation of the cannula with respect to the catheter also biases a distal portion of the pump assembly away from chordae which actuate the mitral valve. This can reduce the chance of the pump assembly being caught therein which could make extracting the pump more difficult.

In implementations in which the rotation angle is achieved by torsioning/twisting the catheter, thermal treatment can set the shape of the catheter. This thermal treatment can occur during sterilization of the catheter during which temperature, pressure, and/or humidity can be cycled to set the shape of the catheter (e.g., by setting the shape of a metal or polymer spine of the catheter). This shape setting occurs as the material is relaxed and/or annealed at a high temperature and then set at a lower temperature. In one example, to form the catheter assembly in an anatomically correct position, the catheter spine is imparted with a rotation angle and/or translation during sterilization which biases the catheter in a desired orientation.

The resulting new, baseline unstressed shape of the catheter, formed by shaping a catheter spine during sterilization or by any of the other methods described herein, reduces the need to apply torque to the catheter during insertion and positioning of the pump assembly within the vessels of the patient (e.g., through the aorta and along the aortic arch). The improved catheter assembly may be helpful for the IMPELLA® 5.0 pump, IMPELLA® 2.5 pump, IMPELLA CP® pump assemblies which are adapted for use in the left ventricle, or may be helpful for any other heart pumps.

Furthermore, the relative position of the cannula and the catheter can be selected to best fit the anatomy of a particular patient or category of patients. This improved fit can also help reduce delivery time.

An unstressed catheter and a cannula rotated or translated away from a proximal portion of the catheter may be presented in a tray (e.g., a packaging tray). Alternatively, an unstressed catheter and a cannula rotated or translated away from a proximal portion of the catheter may be manufactured or presented without a tray. A tray may be configured to apply and maintain torsion in the catheter prior to thermocycling (e.g., sterilization) of the catheter assembly. For example, a first portion of the tray may immobilize a first location on the catheter and a second portion of the tray may immobilize a second location on the cannula such that the cannula is rotated and the distal portion of the cannula is at an angle relative to the plane of the tray, as described above. The tray may include a structure which allows the cannula to lie in a plane which is different from the plane of the catheter and the packaging tray. After the catheter assembly is thermally treated in the desired position, for example a position initially maintained by the two tray portions, the catheter retains its torsion/twisted shape in an unstressed, resting state, and the cannula retains its shape and angular position when the catheter assembly is removed from the tray and during insertion into a patient.

Also disclosed herein are methods of manufacturing a catheter assembly having the configurations described above. According to one method, the proximal catheter portion is held fixed, and the cannula is rotated and/or translated until the cannula is in the desired location relative to the catheter. The cannula is then held fixed and thermocycling is performed. After completion of the thermocycling process, the shape of the catheter is set. In this configuration the catheter is no longer under stress when in the set shape. In another method, the cannula, the catheter, or both are rotated relative to one another to achieve a particular desired angle between the distal portion of the cannula and a reference plane (e.g., the plane of the aortic arch). In some implementations, a handle coupled to the catheter assembly is rotated relative to the catheter assembly or one or more components of the catheter assembly and the shape of the assembly is set.

FIG. 1 shows an illustrative representation of a prior art packaged pump assembly 100. The packaged pump assembly 100 includes a tray 114, a tray portion 116, a flexible atraumatic protrusion, also referred to as pigtail 102, a pump inlet 104, a distal cannula portion 106, a proximal cannula portion 108, a catheter 110, and a catheter end unit 112. The pigtail 102 extends from the inlet 104 which is adjacent to or located on the distal cannula portion 106. The distal cannula portion 106 is angled from the proximal cannula portion 108 by an angle α. For example, the distal cannula portion 106 is angled from the proximal cannula portion 108 by an angle α of about 35°. The proximal portion 108 is connected to the catheter 110, and the proximal portion 108 is aligned with a direction of the catheter 110 such that there is no torsion between the proximal portion 108 and the catheter 110. The proximal portion of the cannula 108 is located at a distance 134 from a principal edge of the tray, which is identical to a distance 132 between a portion of the catheter inside groove 130 and the principal edge of the tray. The proximal portion 106, the distal portion 108, and the catheter 110 lie in the plane of the upper surface of the tray portion 116, which is parallel to the main plane of the packaging tray 114. The catheter 110 is also connected to the catheter end unit 112, which may include a repositioning unit, a plug, an infusion filter, a pressure reservoir and a check valve. The pigtail 102, the distal portion 106, and the proximal portion 108 are located within the tray portion 116 which is recessed relative to the rest of the tray 114. In the configuration shown in FIG. 1 there is no torque applied to any of proximal portion 108, distal portion 106, or catheter 110. The catheter 110 can be made of a polyamide inner layer and a polyurethane outer layer and when the tray 114 is sterilized, the tray 114, the proximal portion 108, the distal portion 106, and the catheter 110 undergo thermocycling which affect the catheter materials. The catheter materials relax when the temperature increases and set when the temperature cools. The shape or spine of the catheter 110 provided by the tray 114 is set by the end of the sterilization process such that when the catheter 110 is removed from the tray 114 (e.g., for use in a procedure), the catheter 110 substantially retains its shape with the distal end of the catheter 110 aligned with the proximal portion 108 of the cannula.

As discussed above, when a catheter (e.g., catheter 100 in FIG. 1) has set in this shape, in some cases it may be necessary to apply torque during placement, but there is a limit on the amount of torque which can be safely applied to the catheter before the catheter recoils. Applying too little force on the catheter makes positioning the pump assembly in the desired location difficult. However, applying too much force on the catheter can result in the applied force being released in an uncontrollable manner and/or can move the pump to an improper position resulting in low flow or suction. Accordingly, a steerable catheter (not shown) may be used to steer the catheter shaft and position the distal cannula portion in the anatomy. Such a steerable catheter may include a steering mechanism in a handle outside a patient's body, which allows for repositioning by steering. However, while a steerable catheter helps direct the cannula in the desired direction upon insertion, it may not allow for repositioning after the initial insertion. Procedures requiring frequent repositioning are again limited by the amount of torque which can be safely applied to the catheter before the applied torque is released in an uncontrollable manner and the catheter recoils. Furthermore, while the steerable catheter helps position the cannula in the desired location, it is limited by the existing shape of the cannula (such as the position of the distal cannula portion 106 relative to the catheter 110).

Figure 2:
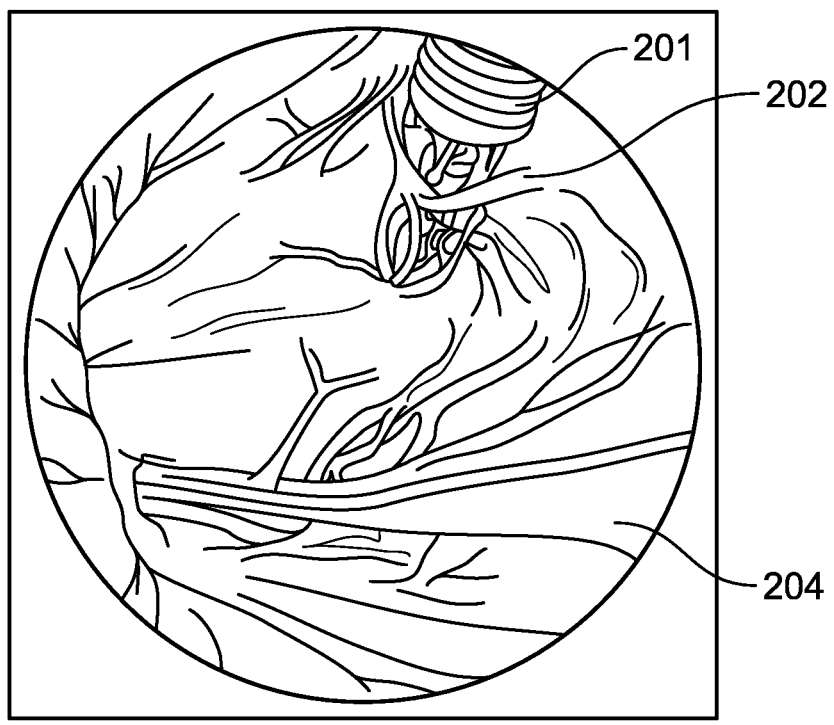
FIG. 2 shows a top-down, partial view of the prior art pump assembly positioned next to a mitral valve.

FIG. 2 shows a top-down view of a conventional pump assembly (e.g., the prior art pump assembly 100 in FIG. 1) in contact with the chordae 202 of the mitral valve 204 during a cadaver study. As discussed above in relation to FIG. 1, the location of the catheter spine in the patient is affected by the way that the pump assembly is held in its packaging tray. And for a conventional tray configuration (e.g., the tray configuration of FIG. 1), the inlet of the pump is biased to sit in or near the mitral valve and its structures when implanted into a patient (as shown in FIG. 2). The pigtail and inlet portion of a conventional pump assembly 201 are tangled with the chordae 202 of the mitral valve 204. This tangling can compromise the position of the inlet of the conventional pump assembly 201, such as by obstructing the inflow leading to low blood flow and decreased circulatory support for the patient.

Figure 3:
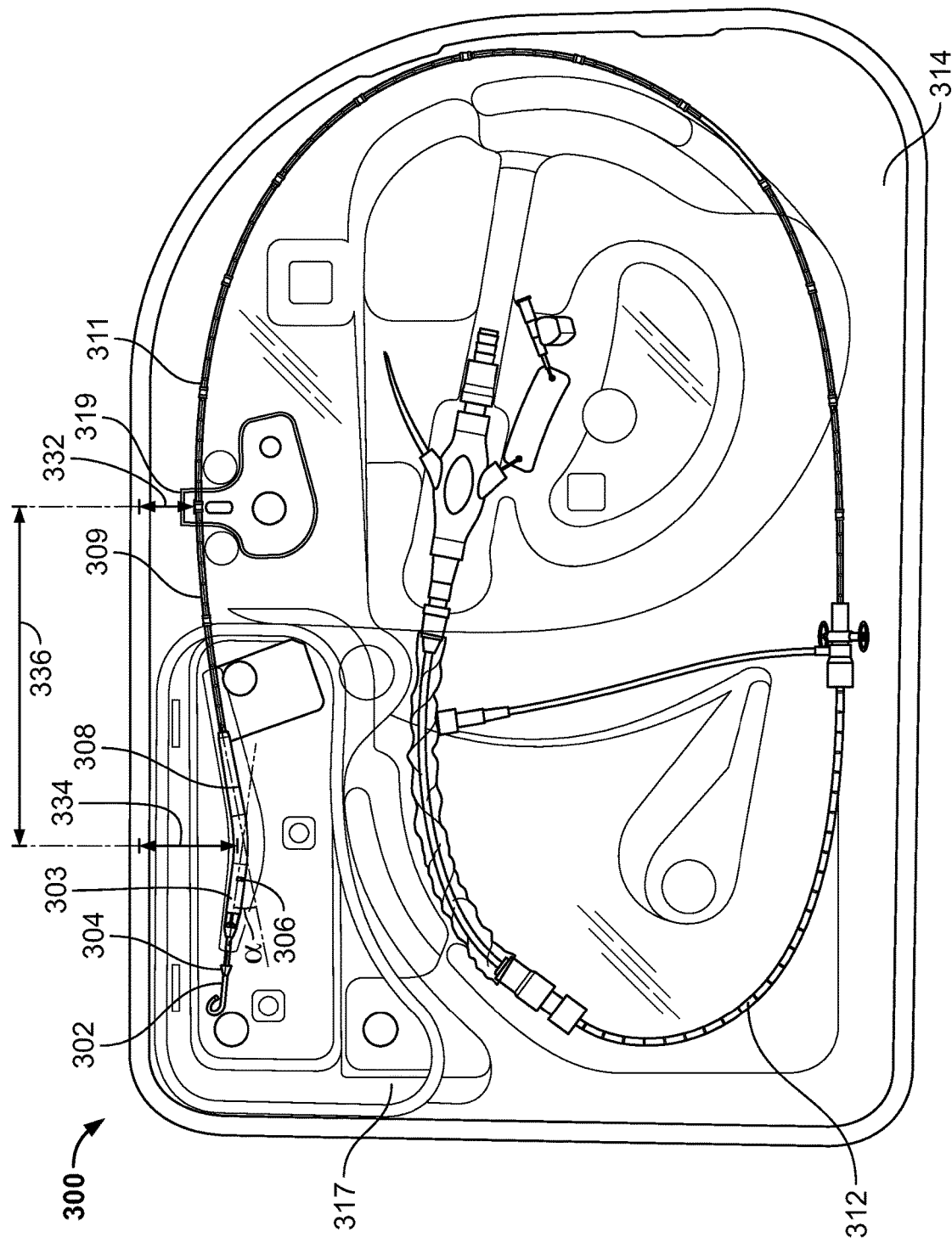
FIG. 3 shows a first illustrative embodiment of a pump assembly having a resting shape that provides a closer anatomical fit than the prior art pump assembly.

FIG. 3 shows a first illustrative embodiment of a packaged pump assembly 300, the pump assembly 300 having a particular shape that facilitates positioning the pump in a patient. The packaged pump assembly 300 includes a tray 314, a first tray portion 317, a second tray portion 319, an inlet 304, a distal cannula portion 306, a proximal cannula portion 308, a catheter transition portion 309, a proximal catheter portion 311, a catheter end unit 312, and a pigtail 302. The pigtail 302 extends from the inlet 304, located on the distal cannula portion 306. The distal cannula portion 306 is angled from the proximal cannula portion 308 (by angle α, shown in FIG. 1). In this example, the distal cannula portion 306 is angled from the proximal cannula portion 308 by an angle α which is substantially 35°. In some implementations, the distal cannula portion 306 is angled from the proximal portion 308 by an angle α which may be 25°, 30°, 35°, 40° or 45°.

The proximal cannula portion 308 and the distal cannula portion 306 are fixed relative to the tray 314 by the first tray portion 317. A midpoint of the cannula between its proximal portion 308 and its distal portion 306 is at a distance 334 from a principal edge of the tray 314. The proximal cannula portion 308 is connected to a catheter transition portion 309, and the catheter transition portion 309 is torsioned between the proximal cannula portion 308 and the second tray portion 319 where the catheter 303 is fixed relative to the tray 314. The catheter 303 may be fixed relative to the tray 314 at a location at a distance 332 from a principal edge of the tray. This distance 332 may be smaller than the distance 334 between the cannula and the principal edge of the tray. Alternatively, the distance 332 may be greater than the distance 334 between the cannula and the principal edge of the tray. The midpoint of the cannula is at a distance 336 from the point where the catheter is fixed. The distance 336 may be equal to 20% of a principal length of the tray. In another example, the distance 336 may be equal to 30%, 40%, 50% or 60% of the principal length of the tray. Alternatively, a distance between the point where the cannula 303 is fixed relative to the tray 314 and a coupling between the cannula 303 and the proximal portion 306 of the cannula is selected to be between 10-60% of a length of the catheter (e.g., 10%, 20%, 30?, 40%, 50%, 60%). The proximal portion 306 and the distal portion 308 of the cannula are in one plane which is at an angular offset from the plane of the packaging tray 314. In another example, the distance 336 may be greater than either the distance 334 and 332.

Figure 8:
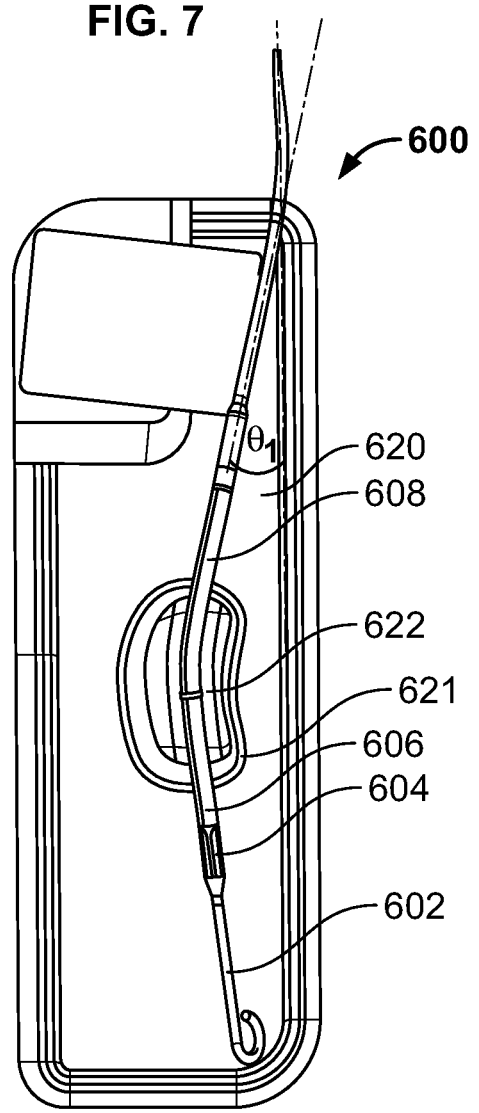
FIG. 8 shows a top view of the first portion of the packaging tray and the pump assembly of FIG. 6.
Figure 9:
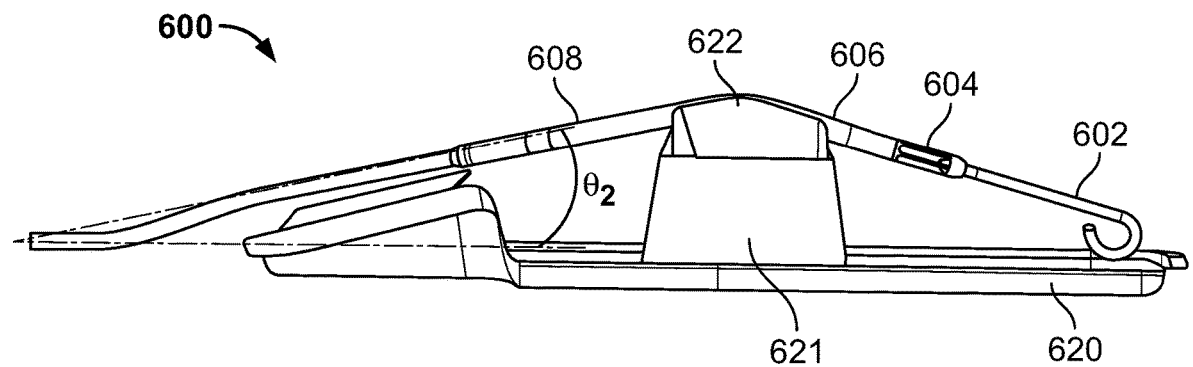
FIG. 9 shows a side view of the first portion of the packaging tray and the pump assembly of FIG. 6.

The angular offset θ2 between the plane of the cannula and the plane of the tray defines the shape of the catheter transition portion 309, as shown in FIG. 9. The translation and/or rotation of the cannula also results in the distal portion of the cannula 308 being rotated in the plane of the packaging tray, and rotated out of the plane of the packaging tray (corresponding to a plane of the aortic arch), as shown in FIGS. 8 and 9. The proximal catheter portion 311 is also connected to the catheter end unit 312, which may include a repositioning unit, a plug, an infusion filter, a pressure reservoir and a check valve.

The proximal and transition portions of the catheter 309, 311 can be have a polyimide inner layer and a polyurethane outer layer. In addition, the catheter of any of the embodiments described in FIG. 3 and FIGS. 12-14 may be braided to increase the amount of torque which can safely be applied once the pump assembly is in place.

When the tray 314 is sterilized, the tray 314, the proximal portion 306, the distal cannula portion 308, the proximal cannula portion 309 and the catheter transition portion 311 undergo thermocycling with changes in temperature and humidity which affect the catheter materials. For example, the temperature may vary between 70° C. and 150° C. above a transition temperature such that the material is soft and elastic. The catheter materials relax when the temperature increases and set when the temperature cools. The shape or spine of the catheter is set by the end of the sterilization process such that when the catheter is no longer in the tray 314 (e.g., when the catheter is in use in a procedure), the catheter substantially retains its shape. For example, the proximal cannula portion 308 being at an angle relative to a plane of the proximal catheter portion 311, and the distal cannula portion 306 being in a plane angled from the plane of an aortic arch. In one example, the shape or spine of the catheter transition portion 309 is set by the end of the sterilization process, such that when the catheter transition portion 309 is no longer in the tray 314 (e.g., when the catheter is in use in a procedure) the catheter substantially retains its shape, the proximal cannula portion 308 is at an angle relative to a plane of the proximal catheter portion 311, and the distal cannula portion 306 is in a plane which is at an angular offset from the plane of an aortic arch.

In certain embodiments, the proximal cannula portion 308 is in a first plane, and the proximal catheter portion 311 is in a second plane which is not parallel to the first plane. An angular offset between the first plane and the second plane is determined based on a desired placement for the cannula and catheter assembly. For example, as described in relation to FIG. 2 above and FIGS. 4-5, 16 and 21 below, a desired anatomical position may be a position which both rotates and translates an inlet of a pump away from a mitral valve of a heart and toward the apex of a left ventricle. In one example, an angle θ2 between a first plane of the proximal cannula portion 308 and a second plane of the proximal catheter portion 311 is 40°. In one example, an angular offset between a plane of the distal cannula portion 306 and a plane of the aortic arch (e.g., the plane of the packaging tray in the exemplary embodiment of FIG. 3) is between 70° and 120°, Preferably, an angular offset between a plane of the distal cannula portion 306 and a plane of the aortic arch is between 80° and 110°. Preferably, an angular offset between a plane of the distal cannula portion 306 and a plane of the aortic arch is about 92°.

As discussed above, when a catheter (e.g., catheter 100 in FIG. 1) has set, for example as a result of thermocycling, it can be difficult to insert a pump assembly into a patient because of the limited amount of torque which can be safely applied to the catheter before the applied torque is released in an uncontrollable manner and the catheter recoils. A packaging tray 314 is one way to allow rotating the distal cannula portion 306 relative to the proximal catheter portion 311, thereby torsioning the catheter transition portion 309 before the pump assembly 300 is positioned in the packaging tray 314. This provides a better anatomical fit of the pump assembly 300 relative to a patient. Configuring the shape of the catheter transition portion 309 in this way also contributes to a reduction in the delivery time because it reduces the risk of the cannula 303 being stuck in the chordae. Alternatively rotation of the distal cannula portion 306 can be carried out even in the absence of a packaging tray, or following the removal of the pump assembly from a packaging tray.

Figure 4:
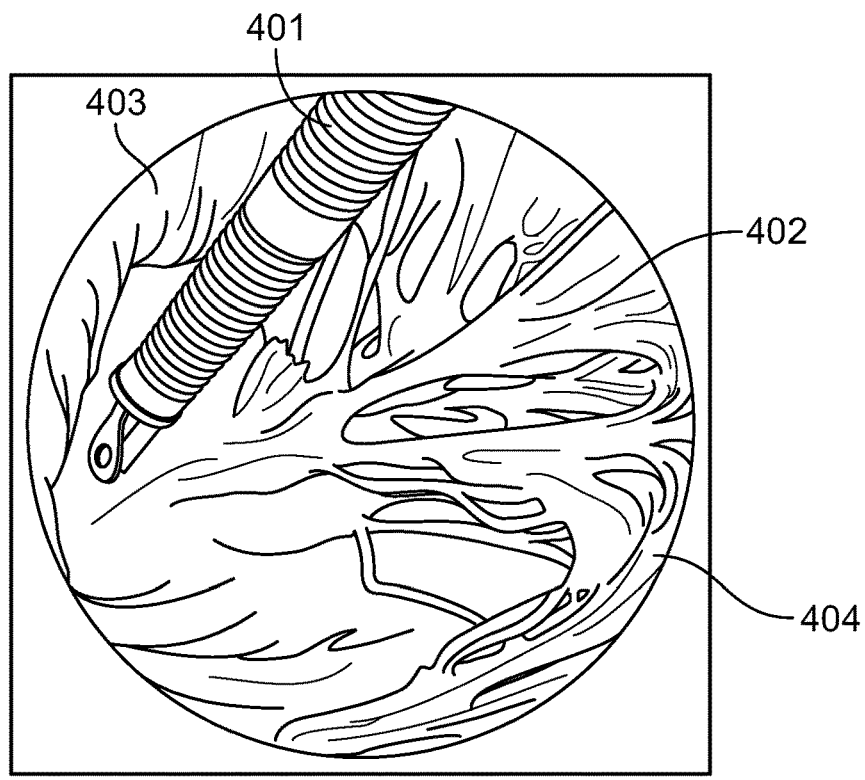
FIG. 4 shows a top-down, partial view of a first illustrative pump assembly positioned next to a mitral valve.

FIG. 4 shows a top-down view of a first illustrative embodiment of a pump assembly at a distance from the chordae 402 of the mitral valve 404 during a cadaver study. As shown, the pigtail and inlet portion of a first illustrative embodiment of a pump assembly 401 are positioned along the side 403 of the mitral valve 404, but free from the chordae 402 of the mitral valve 404 such that the inlet portion will not be obstructed. This can in turn reduce the risk of suction and/or low blood flow through the pump due to improper pump positioning.

Figure 5:
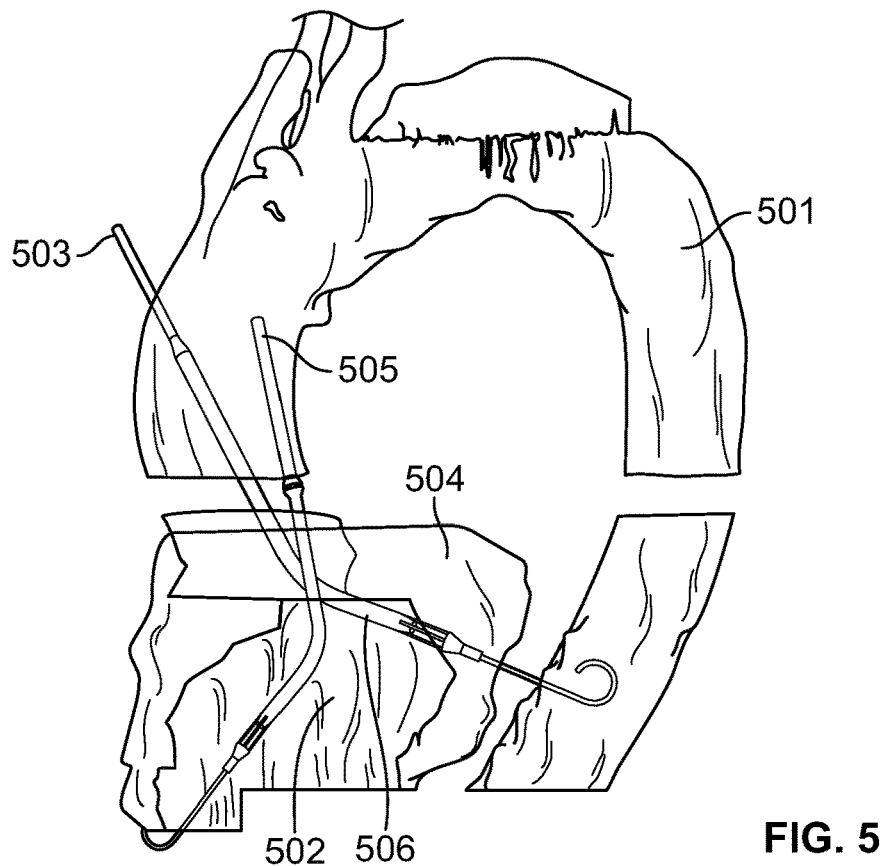
FIG. 5 shows a front, partial view of the prior art pump assembly and the first illustrative embodiment of a pump assembly positioned next to a mitral valve.
Figure 6:
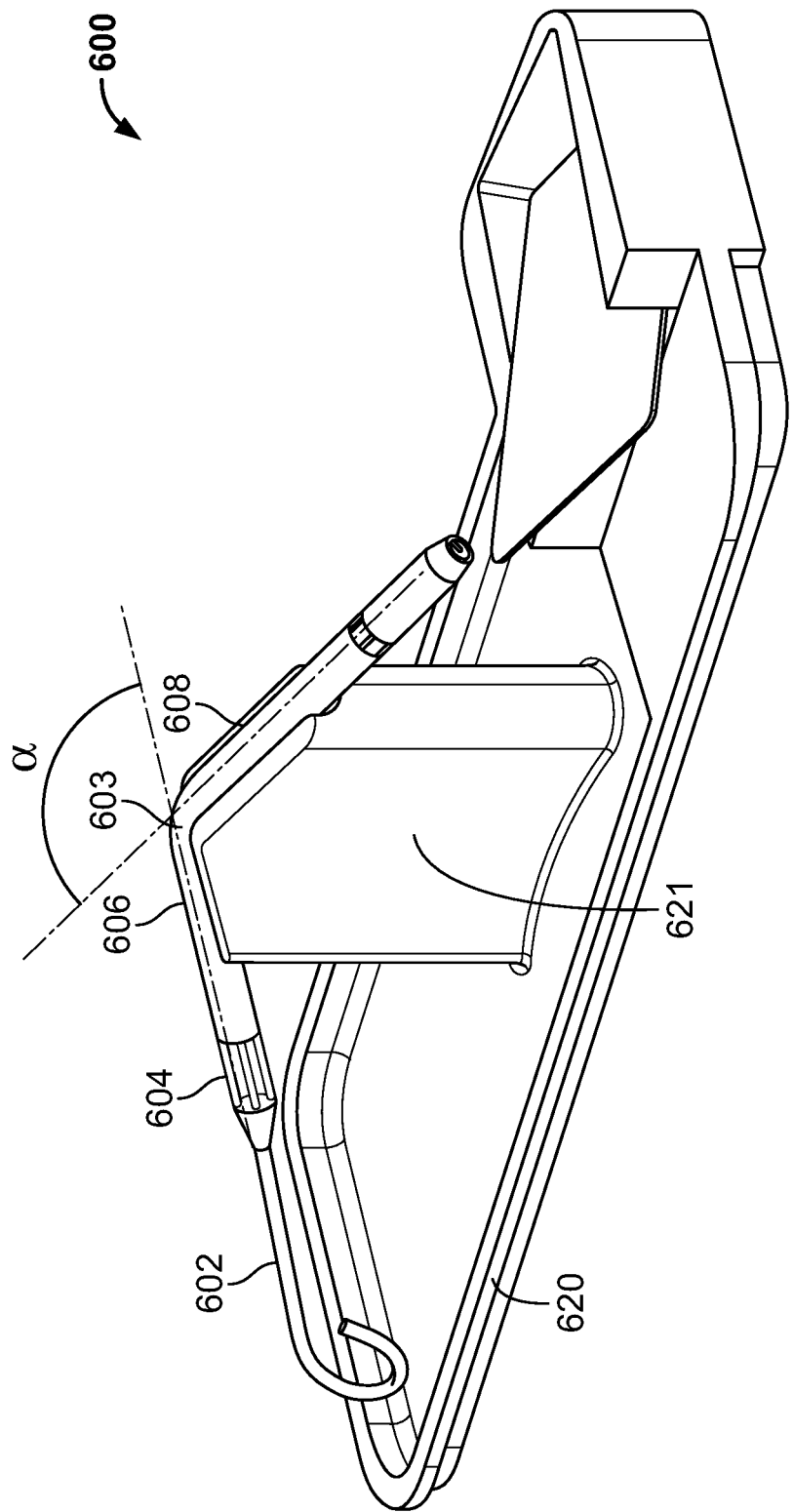
FIG. 6 shows an isometric view of the first illustrative embodiment of a pump assembly in a first portion of a packaging tray configured to hold a cannula out of a plane of the packaging tray.

FIG. 5 shows a front view of a conventional pump assembly and a first illustrative embodiment of a pump assembly positioned across an aortic valve and in the left ventricle. FIG. 5 shows the aorta 501, the mitral valve 504, the chordae 502, a conventional pump assembly 503 and an illustrative embodiment of a pump assembly 505. The pump assemblies 503 and 505 are advanced through the aorta 501 across the aortic valve. When the conventional pump assembly 503 is used, the chordae 502 of the mitral valve interfere with the distal cannula portion 506, as shown also in FIG. 2. In contrast, when the first illustrative embodiment of a pump assembly 505 is positioned therein, the distal cannula portion is shifted away from the chordae 502 of the mitral valve and instead passes through the aortic valve and into the left ventricle.

Figure 17:
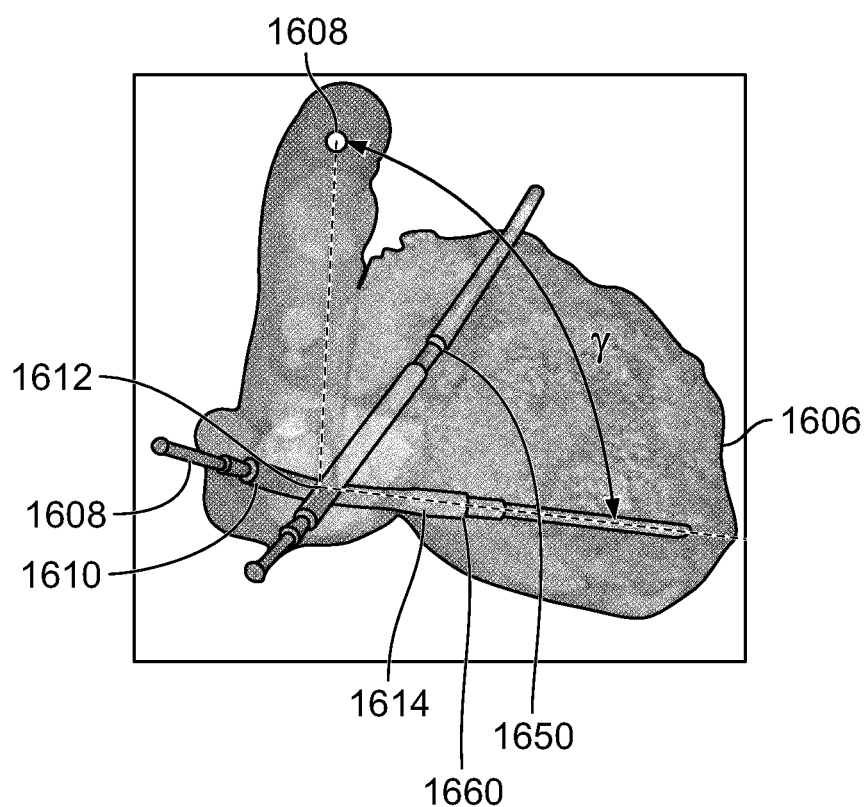
FIG. 17 shows a top down view of the pump assembly shown in FIG. 16.

The angle between the descending aorta direction and the location of the ideal pump placement (e.g., biased away from the mitral valve) was determined using software such as Mimics®. This angle is the desired angle at which the distal portion of the cannula (and the pump) should be positioned relative to a plane of the aortic arch to obtain an assembly shape which provides an anatomical fit. By way of example, the distal portion of the cannula can be angled in a similar way relative to a packaging tray to achieve this shape and provide a closer anatomical fit. The anatomically optimum rotation angle of the distal cannula portion relative to the plane of the aortic arch (as shown in FIG. 17) may depend on patient size and anatomy. Aortic arches differ in size and shape and the size of the ventricle varies based on size and age. In one study, the average rotation angle of the distal cannula portion (and the associated catheter transition portion torsion angle) varied between 125° and 65° respectively, with a preferred angle of 92°. In certain implementations, the rotation angle is 65°, 70°, 75°, 80°, 85°, 90°, 95°, 100°, 105°, 110°, 115°, 120°, or any other suitable angle. In some cases the rotation angle may also be greater than 125° (e.g., 180°) or less than 64° (e.g., 30°).

FIGS. 6-9 show various views of a first portion 600 of a packaging tray which holds a first illustrative pump assembly. The cannula 603 includes a pigtail 602, an inlet 604, a distal portion 606, and a proximal portion 608. An angle θ1 between the proximal portion 608 and an axis of the proximal portion of a catheter is shown at least in FIG. 8. A dihedral angle θ2 between the proximal portion 608 and the plane in which a connected catheter is positioned (e.g., the principal plane of a packaging tray) is shown at least in FIG. 9. The first portion of the packaging tray can include a bottom 620 and a protrusion 621. The bottom 620 may be added to an existing packaging tray as an insert, e.g., placed within the recess 116 of the tray 114 shown in FIG. 1. Alternatively, the bottom 620 may be integral to a packaging tray (e.g., tray 514 shown in FIG. 5). The protrusion 621 is centrally located on the bottom 620 and supports both the distal portion 606 and the proximal portion 608 of the cannula. Alternatively, the protrusion 621 may support one of the proximal portion 608 or the distal portion 606. The top of the protrusion 621 follows the shape of the proximal portion 608 and the distal portion 606 of the cannula. The length of the protrusion 621 may vary between 25% and 75% of the length of the bottom 620. The height of the protrusion 621 may vary, and may be configured such that the pigtail 602 is not in contact with the bottom 620. Alternatively, a shape of the protrusion 621 may be adapted to accommodate a different cannula geometry.

Figure 7:
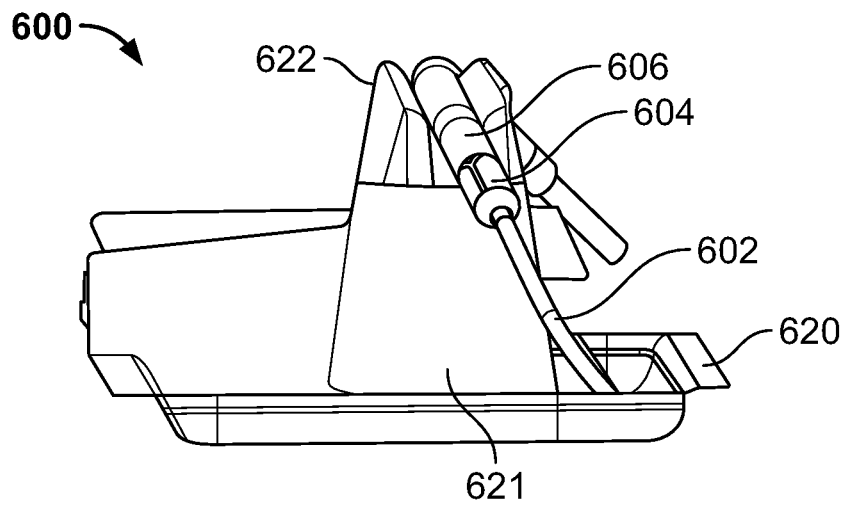
FIG. 7 shows a front view of the first portion of the packaging tray and the pump assembly of FIG. 6.

FIG. 7 shows a front view of the first portion 600 of a packaging tray. The cannula includes a pigtail 602, an inlet 604, a distal portion 606 and a proximal portion 608. The first portion of the packaging tray also includes a recess or ridge 622 which can hold the cannula in a fixed position such as via a press-fit. In any of the embodiments described herein, the ridge may hold a portion or an entire length of the cannula. For example, the ridge may contact over 10%, 20%, 30%, 40%, 50%, 60%, 70%, 80%, 90% of the cannula. In another example, the ridge may be replaced by a groove, such as a 3D printed groove, or a thermoformed cavity configured to grip the cannula.

Figure 10:
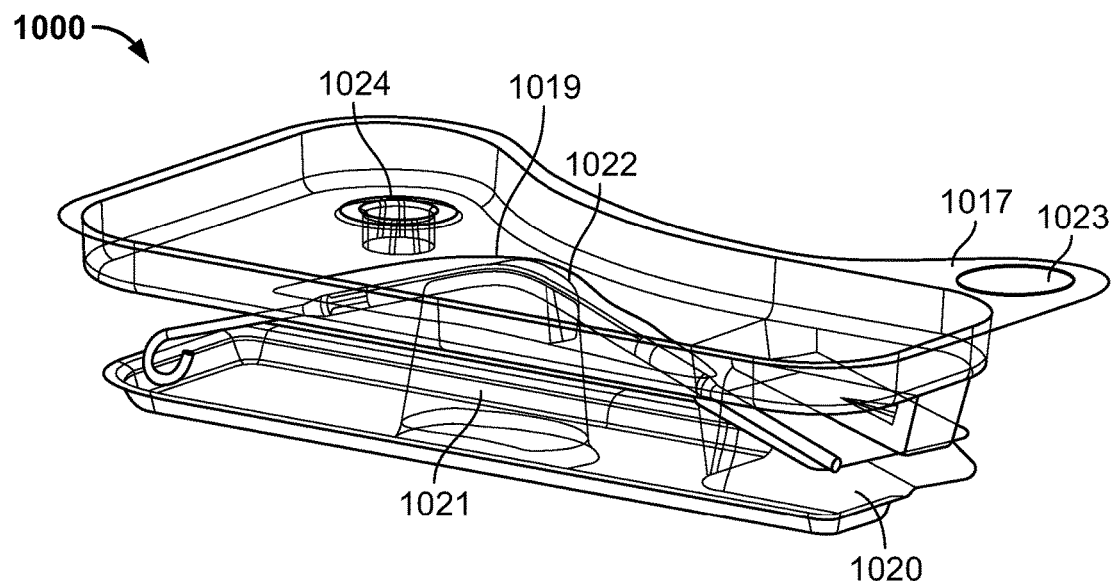
FIG. 10 shows an isometric view of a second illustrative embodiment of a pump assembly in the first portion of a packaging tray and held in place by a cover.

FIG. 10 shows an isometric view of a first portion 1000 of a packaging tray (not shown) which holds a second illustrative embodiment of a pump assembly. The first portion 1000 includes a bottom 1020, a protrusion 1021, a ridge 1022, and a cover 1017 with a protrusion 1022, a protrusion 1024, and a protrusion 1023. The bottom 1020, the ridge 1022, and the protrusion 1021 may be similar to the corresponding components shown in FIGS. 7-9. The cover 1017 provides additional support to keep a cannula in place relative to a packaging tray. A portion of the cannula is clamped between the ridge 1022 and the protrusion 1019 of the cover 1017. The ridge 1022 may be a press-fit ridge. In addition, protrusions 1023 and 1024 may lock with protrusions located on a packaging tray to ensure that there is no movement relative to the packaging tray. Ensuring that the catheter transition portion (not shown) sets in a shape that provides a better anatomical fit can improve ease of use and reduce the time required to deliver and position the pump in the heart and/or can reduce suction and/or low flow events due to improper positioning. An additional means of fixing the cannula 1025 relative to the bottom 1020 provides redundancy and guarantees that the catheter transition portion will set in the desired anatomical position, despite twisting the body of the cannula relative to the catheter.

Figure 11:
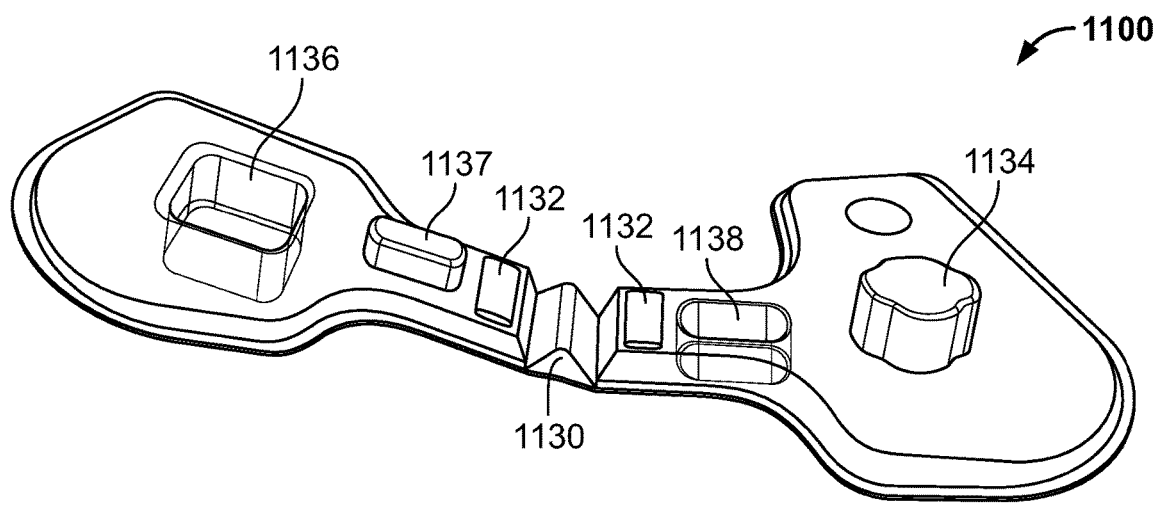
FIG. 11 shows a second portion of a packaging tray configured to hold a proximal portion of a catheter in a fixed position.

FIG. 11 shows a second portion 1100 of a packaging tray in a first illustrative embodiment of a pump assembly configured to hold a cannula therein. The second portion of the packaging tray includes a hinge 1130, grip pads 1132, a protrusion 1137, a protrusion 1134, a protrusion 1136, and a protrusion 1138. Before a catheter transition portion is torqued and the cannula is fixed in place relative to a packaging tray (e.g., as discussed in relation to FIG. 10), a proximal portion of the catheter (e.g., proximal portion 511 in FIG. 5) must also be fixed in place relative to the packaging tray. The second portion 1100 may be integral to the packaging tray, or may be an insert which can be connected to an existing packaging tray. In one example, the second portion is located at a fixed distance from the coupling between the cannula and the catheter. For example, the second portion 1100 is located away from the coupling between the cannula and the catheter by a distance equal to 10% of the catheter length. In another example the distance between the coupling and the second portion may be 20%, 30%, 40% or 50% of the catheter length.

The second portion 1100 may be a butterfly clip with a hinge 1130 which can be closed such that gripping pads 1132 are located below and above the catheter. The gripping pads 1132 may be coated with a slip-resistant or high-friction coefficient material to resist torque applied to the catheter. Outer protrusions 1136 and 1134 fit within one another and secure the second portion 1100 in the clamped position. Similarly, inner protrusions 1137 and 1138 mate to secure the second portion 1100 in the clamped position. In any of the embodiments described herein, the inserts or integral portions of the tray may be replaced by a fitted groove or trough within the tray. For example, a groove may be 3D printed to fit the catheter and hold it in the desired position.

As discussed above, ensuring that a catheter sets in a shape that provides a better anatomical fit contributes to a reduction in the delivery time. In one example, this can be achieved by ensuring that the catheter transition portion sets in a shape that provides a better anatomical fit. The combination of the gripping pads 1132 and both sets of protrusions 1136, 1134 and 1137, 1138 fixes the catheter relative to the packaging tray and guarantees that the catheter transition portion will set in the desired anatomical position, despite the torque or stress applied on the catheter transition portion from rotating the cannula relative to the catheter.

Figure 12:
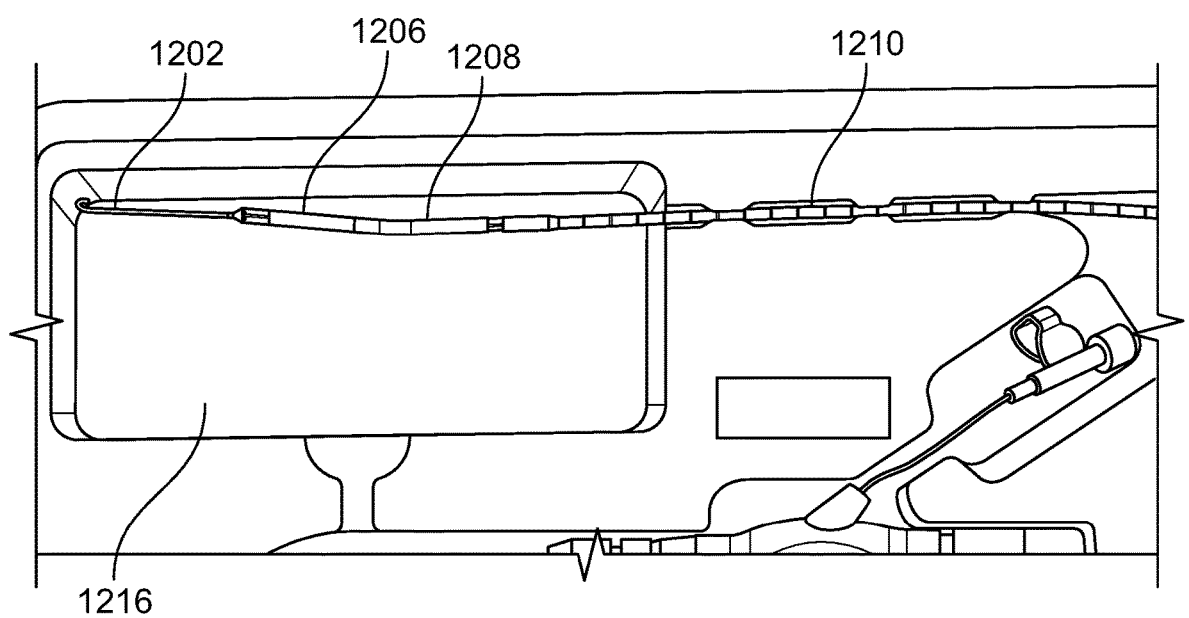
FIG. 12 shows a third illustrative embodiment of a pump assembly in which the cannula is rotated about 90° relative to the catheter, compared to the pump assembly of FIG. 1.

FIG. 12 shows a third illustrative embodiment of a pump assembly. The pump assembly includes a tray portion 1216, a pigtail 1202, a distal cannula portion 1206, a proximal cannula portion 1208, and a catheter transition portion 1210. This third illustrative embodiment is similar to the embodiment shown in FIG. 5, except that the cannula is rotated 90° relative to the catheter such that the catheter transition portion 1210 is torsioned by 90°. The first and second portions of the packaging tray which hold the cannula and the catheter in place, respectively, are omitted for clarity. Rotating the cannula 90° relative to the catheter provides a different anatomical fit for the catheter transition portion, which may be beneficial for certain patient anatomies. The 90° rotation also shifts the pigtail away from the tray and may prevent damage to the pigtail in the packaging.

Figure 13:
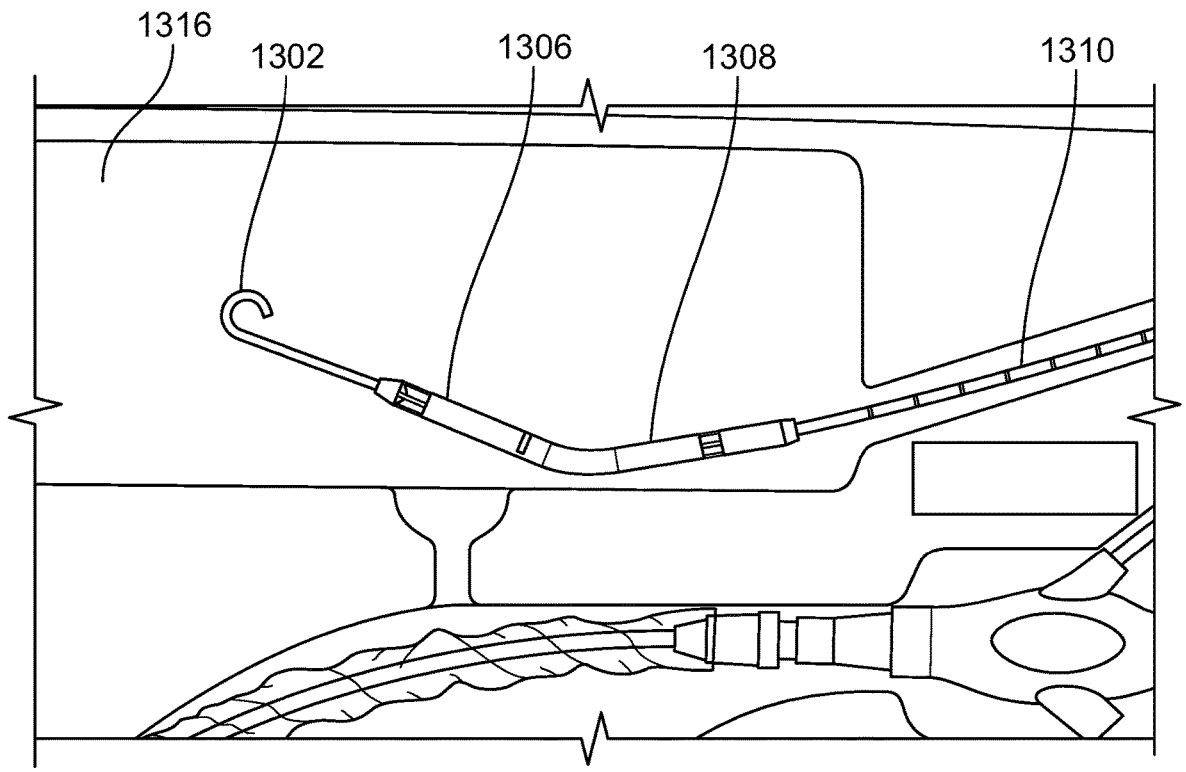
FIG. 13 shows a fourth illustrative embodiment of a pump assembly in which the cannula is rotated about 180° relative to the catheter, compared to the pump assembly of FIG. 1.

FIG. 13 shows a fourth illustrative embodiment of a pump assembly. The pump assembly includes a tray portion 1316, a pigtail 1302, a distal cannula portion 1306, a proximal cannula portion 1308, and a catheter transition portion 1310. This fourth illustrative embodiment is similar to the embodiment shown in FIG. 5, except that the cannula is rotated 180° relative to its conventional positioning (e.g., the position of the prior art cannula shown in FIG. 1). In this exemplary embodiment, the distal cannula portion 1306 is in the same plane as the plane of the catheter 1310, which is parallel to the plane of the packaging tray portion 1316). However, the catheter transition portion 1310 is torsioned by 180° relative to the proximal catheter portion (not shown) within the plane of the packaging tray portion 1316. The first and second portions of the packaging tray which hold the cannula and the catheter in place, respectively, are omitted for clarity.

Figure 14:
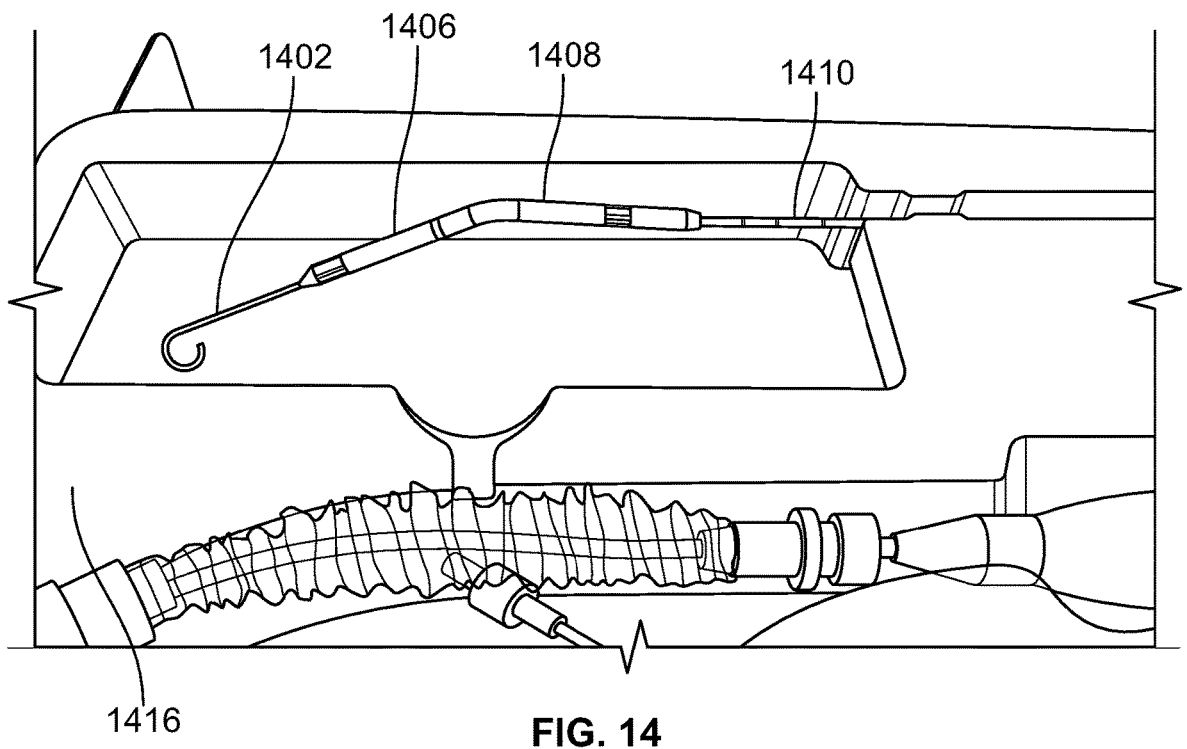
FIG. 14 shows a fifth illustrative embodiment of a pump assembly in which the cannula is rotated about 270° relative to the catheter, compared to the pump assembly of FIG. 1.

FIG. 14 shows a fifth illustrative embodiment of a pump assembly. The pump assembly includes a tray portion 1416, a pigtail 1402, a distal cannula portion 1406, a proximal cannula portion 1408, and a catheter transition portion 1410. This third illustrative embodiment is similar to the embodiment shown in FIG. 5, except that the distal cannula portion 1408 is rotated 270° relative to the catheter proximal portion (not shown) and the catheter transition portion is torsioned by 270° relative to the catheter proximal portion (not shown). The first and second portions of the packaging tray which hold the cannula and the catheter in place, respectively, are omitted for clarity.

Figure 15:
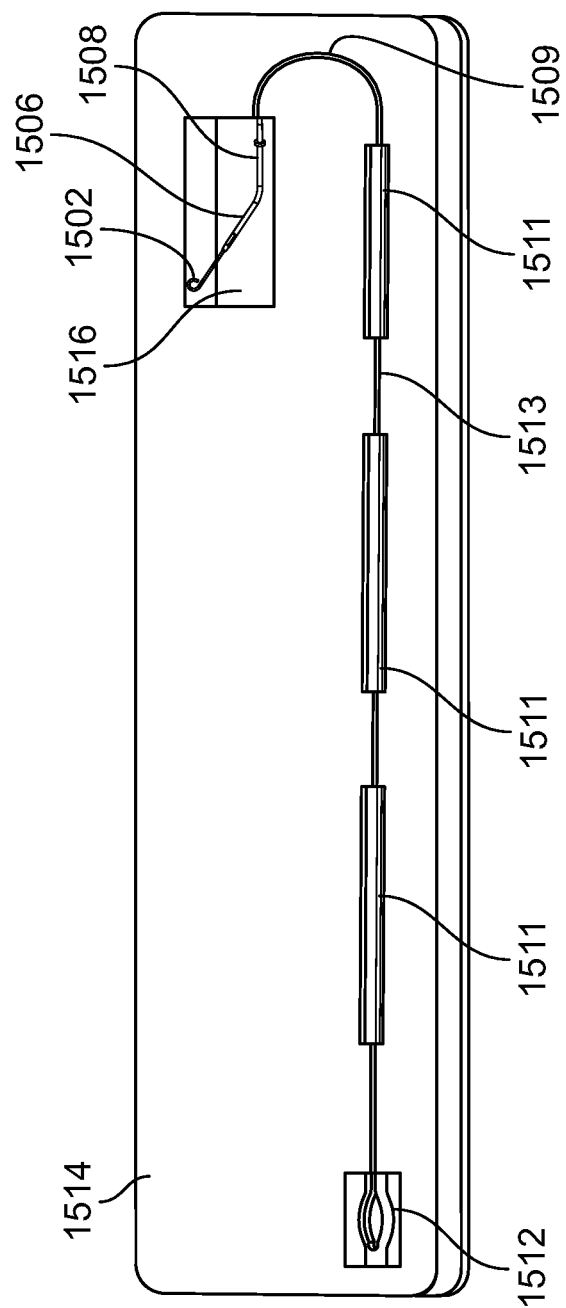
FIG. 15 shows a sixth illustrative embodiment of a pump assembly having proximal and distal cannula portions held at a particular angle and having a transition portion of the catheter set in a curved shape that mimics an angle of an aortic arch.

FIG. 15 shows a sixth illustrative embodiment of a pump assembly. The pump assembly includes a packaging tray 1514, a tray portion 1516, a pigtail 1502, a distal cannula portion 1506, a proximal cannula portion 1508, a first catheter portion 1509, a second catheter portion 1513, a second tray portion 1511 with multiple elements, and a catheter end unit 1512. The pigtail 1502 extends from the distal cannula portion 1506. The distal cannula portion 1506 is angled from the proximal cannula portion 1508. For example, the distal cannula portion 1506 is angled from the proximal cannula portion 1508 by an angle α of 35°. In some implementations, the distal cannula portion 1506 is angled from the proximal portion 1508 by an angle α between 25° and 45°.

The proximal cannula portion 1508 and the distal cannula portion 1506 are fixed relative to the tray 1514 by a first tray portion (not shown) in the recessed tray portion 1516. The proximal cannula portion 1508 is connected to a catheter transition portion 1509, and the catheter transition portion 1509 is torsioned between the proximal cannula portion 1508 and the second tray portion 1511 where the catheter is fixed to the tray 1514. As in the embodiments shown in FIG. 5 and FIGS. 12-14, the proximal cannula portion 1508 may be angled from the plane of the packaging tray 1514 by an angle θ2 (e.g., shown in FIG. 9). The angle θ2 between the proximal portion of the cannula 1508 and the plane of the tray, the angle θ1 (e.g., shown in FIG. 8) and the catheter torsion angle define the shape of the catheter transition portion 1509. In addition, the position of the multiple elements of the second tray portion 1511 may be configured to achieve a "packaged-in-place" configuration such that the majority of the length of the catheter forms a straight line and the curvature of the catheter transition portion 1509 in the plane of the packaging tray simulates the curve of the aortic arch.

The proximal catheter portion 1513 is also connected to the catheter end unit 1512, which may include a repositioning unit, a plug, an infusion filter, a pressure reservoir and a check valve. The catheter end unit 1512 may also be rotated relative to the proximal portion of the catheter 1513 to reduce the torque applied on the proximal catheter portion in the tray prior to sterilization.

Figure 16:
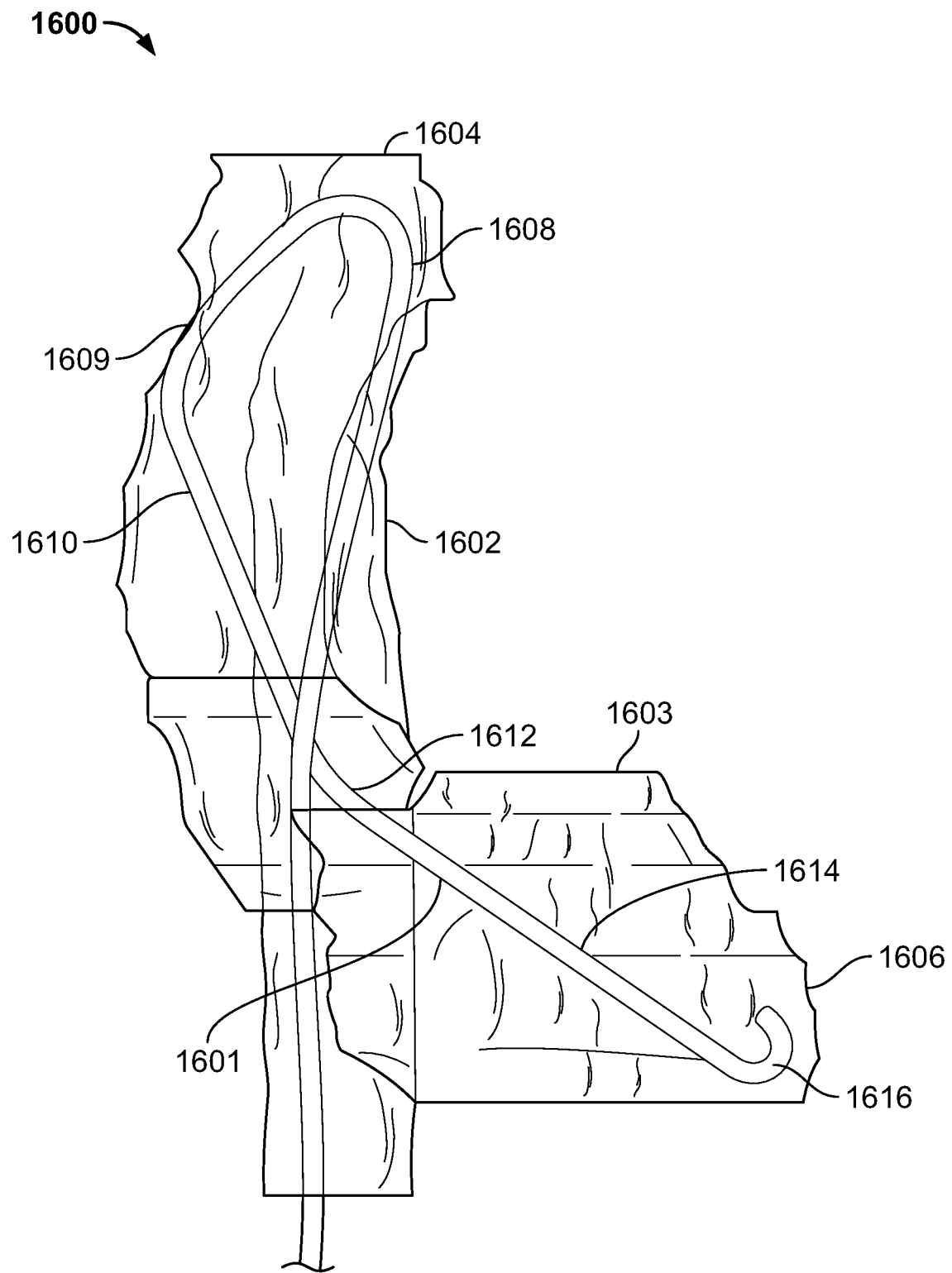
FIG. 16 shows a front view of the first illustrative embodiment of a pump assembly positioned within the left ventricle and aortic arch of a patient.

FIG. 16 shows a seventh illustrative embodiment of a pump assembly 1601 located in a heart 1603, and FIG. 17 shows a top down view of the pump assembly 1601. The pump assembly 1601 includes a pigtail 1616, a distal cannula portion 1614, a proximal cannula portion 1610, a bend 1612 between the distal cannula portion 1614 and the proximal cannula portion 1610, proximal catheter portion 1608 and distal catheter portion 1609. The heart 1603 includes a ventricle apex 1601, aorta 1602, and the aortic arch 1604. The pigtail 1616 extends from the distal cannula portion 1614 and is located near the ventricle apex 1601. The catheter portion 1608 follows the aorta 1602 and the aortic arch 1604. The catheter portion 1609 located after the aortic arch is connected to the proximal cannula portion 1610. The bend in the cannula 1612 is located between the proximal cannula portion 1610 and the distal cannula portion 1614. An angular offset γ shown in FIG. 17 is the angular offset between a first plane containing the distal cannula portion 1614, and a second plane containing the catheter (catheter portions 1608 and 1609) with the apex of angular offset γ being the bend in the cannula 1612. When the distal cannula portion 1614 is inserted in the heart 1603 via the aorta 1602 and aortic arch 1604, with the distal cannula portion 1604 in the first plane, the curve of the longitudinal axis of the catheter portion (encompassing the proximal catheter portion 1608 and the distal catheter portion 1609) lies in the second plane. The proximal cannula portion 1610 also lies within the second plane.

As shown, the distal cannula portion 1614 is placed such that it points towards the ventricle apex 1606. For reference, FIG. 17 shows an exemplary placement of a cannula 1650, and a cannula 1660 in an alternate cannula placement with the angular offset γ between the plane containing the catheter (catheter portions 1608 and 1609) and the plane containing the distal cannula portion 1614 of the cannula 1660. As shown in FIGS. 16 and 17, the distal portion of the cannula 1614 of the cannula 1660 and the catheter portion 1608 are in different planes and the angular offset γ between the plane of the aortic arch 1604 and the plane of the proximal cannula portion 1610 of the cannula 1660 and the distal cannula portion 1614 of the cannula 1660 biases the cannula 1660 toward the ventricle apex 1601. The rotation of the distal cannula portion 1614 relative to the catheter portion 1608 biases the distal cannula portion 1614 away from the chordae which actuate the mitral valve, thereby reducing the chance of the pump assembly 1601 being stuck following delivery to the left ventricle through the aortic valve. This rotation can also reduce the occurrence of suctioning of the heart wall and/or biomaterial ingestion by the pump assembly 1601.

Figure 18:
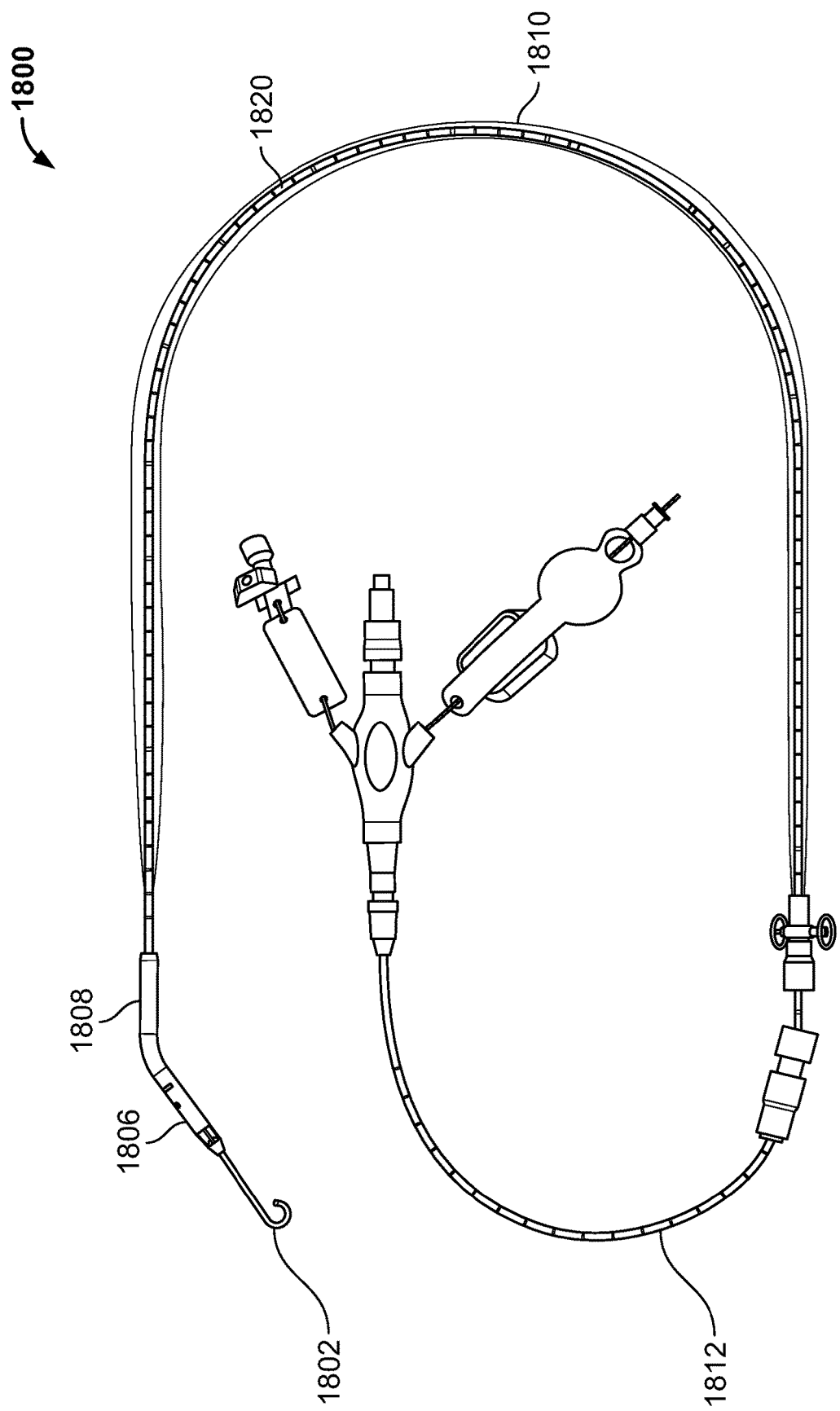
FIG. 18 shows an eighth illustrative embodiment of a pump assembly, the pump assembly having a pre-shaped backbone which affects the resting shape of the catheter.

FIG. 18 shows an eighth illustrative embodiment of a pump assembly. The pump assembly includes a pigtail 1802, a distal cannula portion 1806, a proximal cannula portion 1808, a catheter portion 1810, a catheter end unit 1812, and a backbone 1820. The pigtail 1802 extends from the distal cannula portion 1806. The backbone 1820 may be a pre-shaped, internal or external backbone. For example, the backbone may be made of Nitinol, or a similar shape-memory material. The backbone 1820 may run through the entire length of the catheter portion 1810 and provide stability and shape memory for the catheter portion 1810. Imparting a rotation angle on the distal cannula portion 1806 by pre-shaping the catheter backbone 1820 can allow the rotation angle to be achieved with relatively minor modifications to existing manufacturing processes. For example, in some embodiments, preforming the backbone requires fewer changes to the manufacturing process than rotating the catheter during sterilization.

Figure 19:
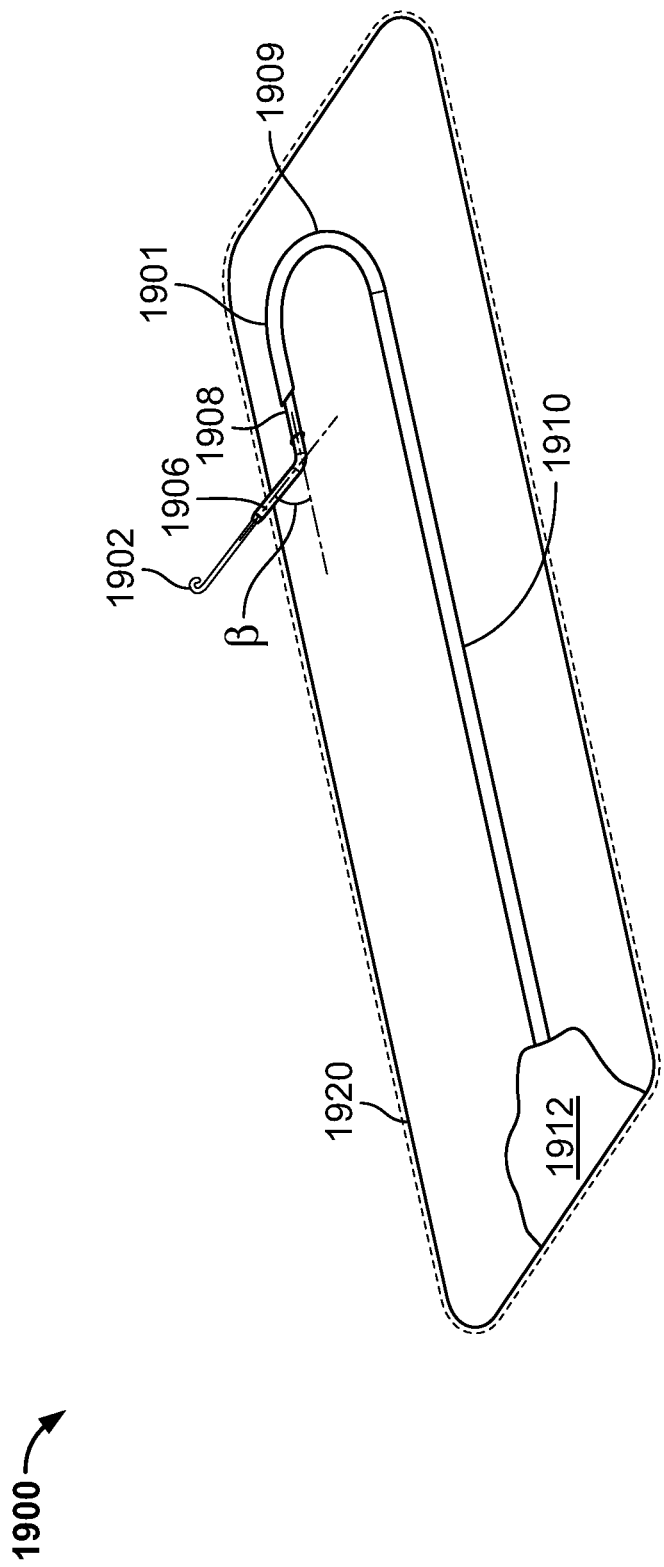
FIG. 19 shows a ninth illustrative embodiment of a pump assembly having a first substantially straight catheter portion and a second curved catheter portion.

FIG. 19 shows a ninth illustrative embodiment of a pump assembly. The pump assembly 1901 is shown in an illustrative plane 1920, and includes a pigtail 1902, a distal cannula portion 1906, a proximal cannula portion 1908, a distal catheter portion 1909, a proximal catheter portion 1910, and a catheter end unit 1912 (details not shown). The illustrative plane 1920 is the plane in which the curve of the longitudinal axis of the catheter portion (encompassing the proximal catheter portion 1909 and the distal catheter portion 1910) lies in a resting state. The proximal cannula portion 1908 also lies in the illustrative plane 1920 in the resting state. The pigtail 1902 extends from the distal cannula portion 1906 and is angled out of the plane of illustrative plane 1920 by angle β. The proximal catheter portion 1910 may be kept substantially straight, and the distal catheter portion 1909 may be shaped for an anatomical fit. For example, the distal catheter portion 1909 may be shaped in the plane 1920, which may be a plane of the aortic arch in a patient. Shaping of the distal catheter portion 1909 may be done in combination with using a packaging tray (e.g., packaging tray 314 from FIG. 3), or without using a packaging tray. The shaping of the distal catheter portion 1909 may be done as an integral step of the manufacturing process, or may be an additional step performed on an already manufactured pump assembly. For example, the distal catheter portion 1909 may be shaped over the aortic arch in a manner similar to that use to shape a JL4 catheter. To pre-shape the catheter, the catheter may be annealed at a temperature between 50° C. and 80° C., preferably at 60° C. As a result of the shaping of the distal catheter portion 1909, the distal cannula portion 1906 may be positioned out of reference plane 1920. For example, as described in relation to FIGS. 16 and 17, the distal cannula portion 1906 may be positioned at an angle relative to the plane of the aortic arch such that the distal cannula portion points the pigtail 1902 towards the apex of a ventricle. Positioning the distal cannula portion 1906 out of the reference plane 1920 by preshaping the distal catheter portion 1909 over the aortic arch can facilitate insertion of the pump assembly 1901, by biasing the distal cannula portion 1906 away from the chordae which actuate the mitral valve, thereby reducing the chance of the pump assembly 1901 being stuck following delivery to the left ventricle through the aortic valve.

Figure 20:
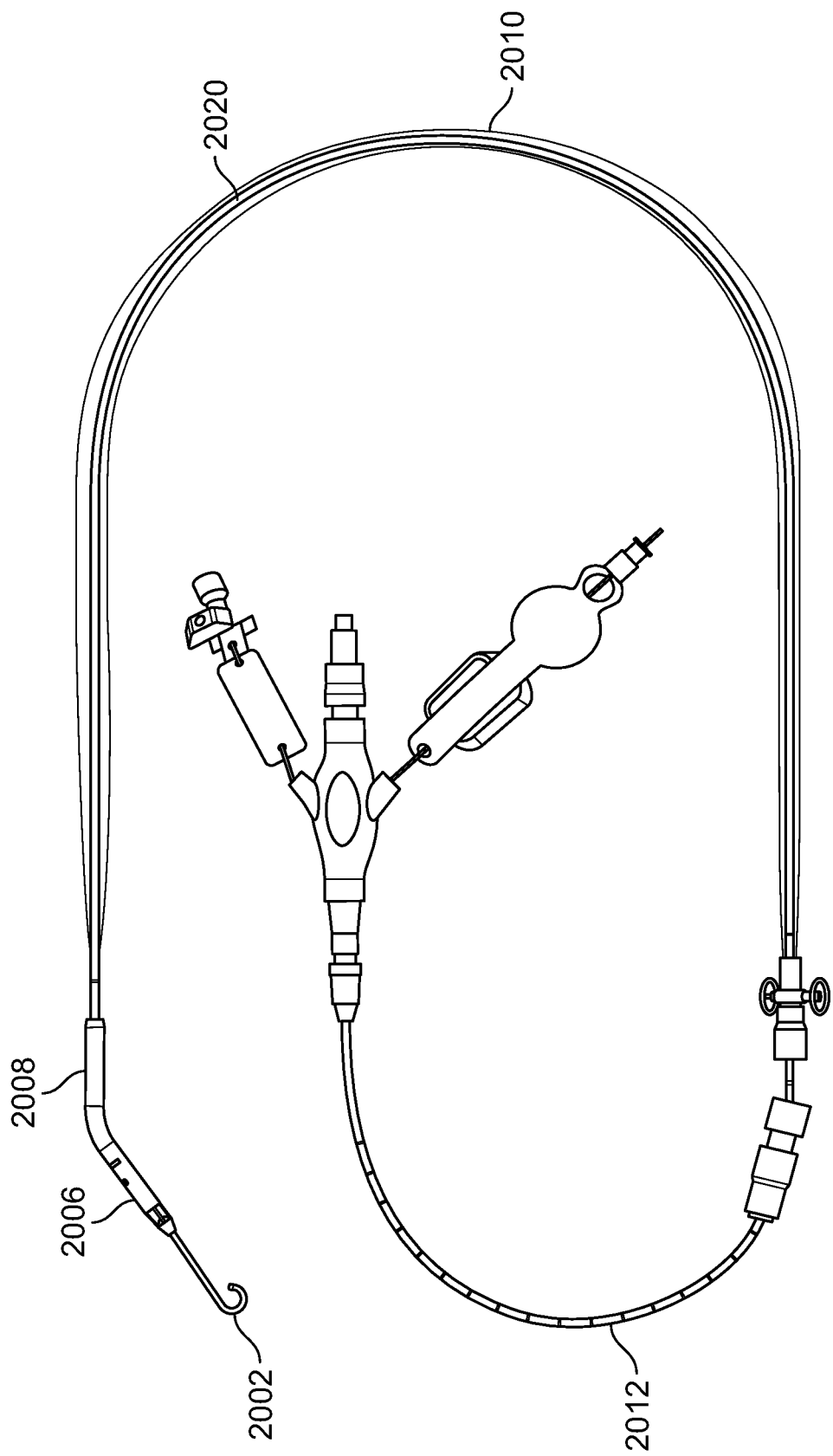
FIG. 20 shows a tenth illustrative embodiment of a pump assembly having a stylet inserted through the catheter and configured to adjust the resting shape of the catheter.

FIG. 20 shows a tenth illustrative embodiment of a pump assembly. The pump assembly includes a pigtail 2002, a distal cannula portion 2006, a proximal cannula portion 2008, a catheter portion 2010, a catheter end unit 2012, and at least one stylet 2020. The pigtail 2002 extends from the distal cannula portion 2006. The at least one stylet 2020 is a geometry altering wire inserted into the catheter portion 2010, and may be used to adjust the catheter portion 2010 to obtain an anatomical fit for a specific anatomy. For example, stylet 2020 may be used to adjust the shape of a distal portion of the catheter portion 2010 such that the distal portion of the cannula 2002 is biased at an angle from the plane of the aortic arch in which the catheter portion 2010 is located. Such an angle is shown for example, in the exemplary embodiments of FIGS. 16 and 17. Different types of stylets 2020 may be used in this exemplary embodiment. For example, the stylet 2020 may be made of a metal or a polymer. This exemplary embodiment with the stylet 2020 may be used instead of, or in combination with the pre-shaped backbone of the exemplary embodiment shown in FIG. 18. Multiple stylets 2020 with different shapes may be used in succession until the distal cannula portion 2006 is located in the desired position.

Figure 21:
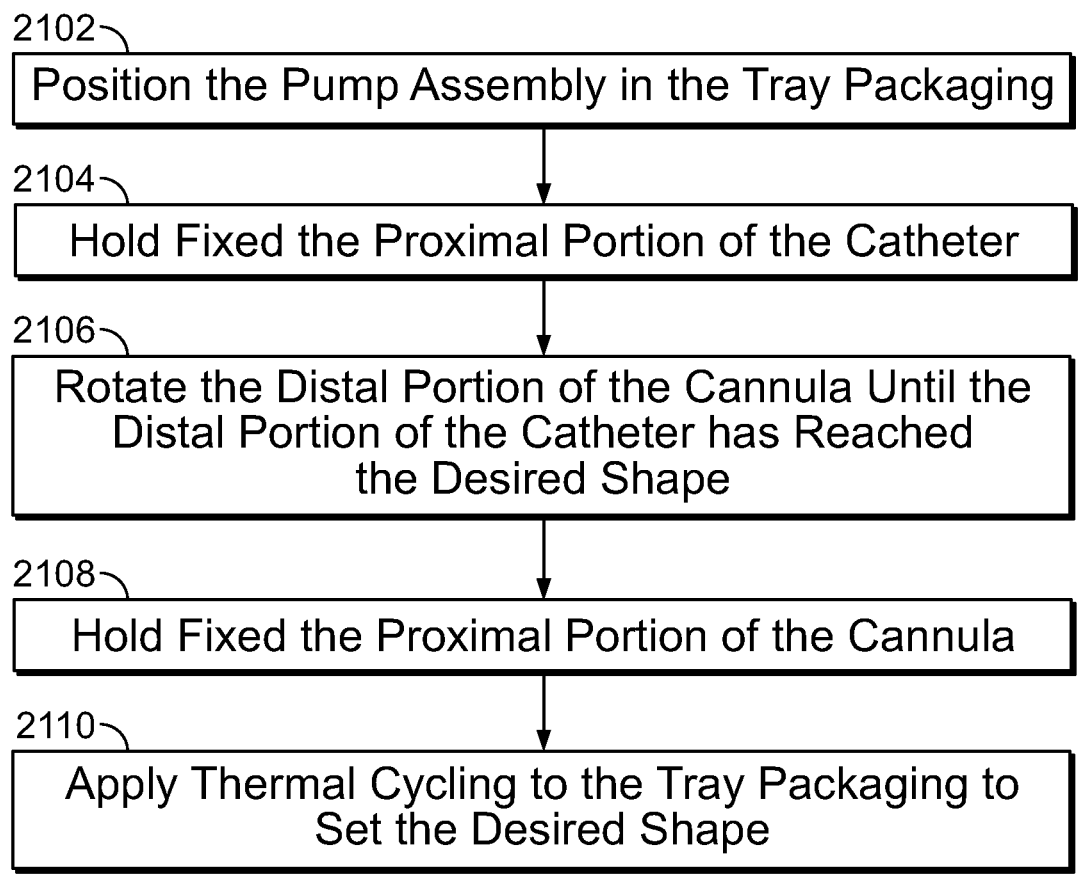
FIG. 21 shows an illustrative process for configuring a resting shape of a pump assembly.

FIG. 21 shows an illustrative method 2100 for configuring a resting shape of a pump assembly, such as one of the illustrative embodiments shown in FIGS. 5-15. The method 2100 may be implemented to configure a catheter which is part of a pump assembly (e.g., pump assembly 100 shown in FIG. 1) including but not limited to the pump assemblies described in any of the aforementioned implementations in FIGS. 5-15. The catheter and cannula may have a resulting resting shape which matches the anatomy of the left ventricle and aortic arch of a patient.

In step 2102, the pump assembly is positioned in the tray packaging. The pump assembly may include a cannula with a proximal portion and a distal portion, and a catheter with a proximal portion and a cannula transition portion, which may be distal relative to the proximal portion. In step 2104, the proximal catheter portion is held fixed relative to the packaging tray. The proximal catheter portion may be held fixed with an integral portion of the packaging tray, or an insert added to the packaging tray. For example, a trough or groove may be 3D printed or formed within the tray to hold the catheter in the desired position. Alternatively, an insert may be used such as a butterfly clip or any other suitable clip or gripping element capable of resisting torque.

In step 2106, the pump assembly is rotated while the proximal catheter portion is held fixed, which torsions the catheter transition portion. The pump assembly is rotated while the proximal catheter portion is held fixed, until the catheter transition portion has reached the desired shape and desired torsion angle. The torsion angle of the catheter transition portion may be about equal to or greater than an angle between an axis of a descending aorta and a predetermined cannula placement location. The torsion angle may vary between 125° and 64° (e.g., 65°, 70°, 75°, 80°, 85°, 90°, 95°, 100°, 105°, 110°, 115°, 120°, or any other suitable angle). The preferred torsion angle may be 92°. In some implementations, the torsion angle may be greater than 125° (e.g., 180°) or less than 64° (e.g., 30°). The packaging tray may be adjustable to allow the torsion angle to be chosen to suit the anatomy of a particular patient or category of patients. As described above in relation to θ1 and θ2, the cannula may also be translated relative to the axis of the proximal catheter portion, and relative to the plane of the packaging tray.

In step 2108, the now-rotated and translated proximal cannula portion is fixed relative to the packaging tray. The proximal cannula portion may be held fixed with an integral portion of the packaging tray, or an insert added to the packaging tray, and the distal cannula portion is held fixed relative to the packaging tray with an integral portion of the packaging tray or an added insert. Fixing both the cannula and the proximal catheter portions relative to the packaging tray as described in steps 2104 and 2108 ensures that the catheter transition portion will retain the desired torsion during thermocycling. In an alternative embodiment, any of the inserts may be replaced by a trough or groove formed within the tray to hold the catheter in the desired position. For example, the groove may be 3D printed or may be the result of a heat molding process.

In step 2110, thermocycling is applied to the tray packaging containing the pump assembly. Once thermocycling is complete the pump assembly will be set in the desired shape. For example, the temperature may vary between 70° C. and 50° C. above a transition temperature such that the material is soft and elastic. Depending on the material, the temperature used during thermocycling may vary between −40° C. and 70° C. (e.g., −40° C., −30° C., −20° C., −10° C., 0° C., 10° C., 20° C., 30° C., 40° C., 50° C., 60° C., 70° C., or any other suitable temperature) The preferred temperature range may be −20° C. and 50° C. (e.g., −20° C., −15° C., −10° C., −5° C., 0° C., 5° C., 10° C., 15° C., 20° C., 25° C., 30° C., 35° C., 40° C., 45° C., 50° C.). The catheter materials relax when the temperature increases and set when the temperature cools. The shape or spine of the catheter, and in particular the shape of the catheter transition portion is set by the end of the sterilization process, such that when the catheter transition portion is no longer in the tray (e.g., when the catheter is in use in a procedure) the catheter transition portion substantially retains its shape.

Use of the packaging tray allows the catheter transition portion to be torsioned such that the cannula is rotated and translated into a position that is a better anatomical fit and can thereby reduce the time for delivery into a patient. Torsioning the catheter transition portion also contributes to a reduction in the delivery time because it reduces the likelihood of the cannula being stuck in the chordae during insertion.

Variations and modifications will occur to those of skill in the art after reviewing this disclosure. For example, in some implementations, any of the embodiments described in FIGS. 3 and 6-20 may be combined. For example, the first portion of the packaging tray of FIGS. 6-9 and the second portion of the packaging tray of FIG. 10 may be confined with different pump assembly packaging configurations described with respect to FIGS. 12-15. In another example, features described with respect to FIGS. 16-21 may be combined with any of the embodiments described in FIGS. 3 and 6-21, with or without a packaging tray. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

It is important to note that the constructions and arrangements of apparatuses or the components thereof as shown in the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative implementations. Other substitutions, modifications, changes and omissions may also be made in the design, operating conditions and arrangement of the various exemplary implementations without departing from the scope of the present disclosure.

While various inventive implementations have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive implementations described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

For the purpose of this disclosure, the termed "coupled" means the joining of two members directly or indirectly to one another. Such joining may be stationary or moveable in nature. Such joining may be achieved with the two members or the two members and any additional intermediate members being integrally formed as a single unitary body with one another or within the two members of the two members and any additional intermediate members being attached to one another. Such joining may be permanent in nature or may be removable or releasable in nature.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

Examples of changes, substitutions, and alterations are ascertainable by one skilled in the art and could be made without departing from the scope of the information disclosed herein. All references cited herein are incorporated by reference in their entirety and made part of this application.

We claim:

1. A catheter assembly of a heart pump comprising:
   a catheter including a proximal catheter portion and a distal catheter portion; and
   a cannula coupled to the distal catheter portion, the cannula having a proximal cannula portion and a distal cannula portion extending from a pre-formed bend between the proximal cannula portion and the distal cannula portion, the proximal cannula portion including a blood pump outlet and the distal cannula portion including a blood pump inlet;
   wherein, the catheter assembly as formed has a predetermined shape when in a resting state,
   wherein, the predetermined shape is configured such that, in the resting state:
      the catheter has a pre-formed curve encompassing the distal catheter portion and at least a portion of the proximal catheter portion;
      the proximal cannula portion and the pre-formed curve of the catheter define a first plane, and
      the pre-formed curve of the catheter is configured such that the distal cannula portion extends out of the first plane at an angular offset relative to the first plane, wherein the angular offset is approximately equal to an angle between:
      (a) a second plane representative of a plane of an aortic arch defined by an ascending portion of an aorta and a descending portion of the aorta, and
      (b) a third plane representative of a plane of the ascending portion of the aorta and an apex of a left ventricle of a patient's heart.

2. The catheter assembly of claim 1, wherein the angular offset is between 64° and 125°.

3. The catheter assembly of claim 2, wherein the angular offset is 92°.

4. The catheter assembly of claim 1, further comprising a stylet inserted into the catheter to adjust a shape of the distal catheter portion.

5. The catheter assembly of claim 1, further comprising a catheter handle connected to the proximal catheter portion and rotated to adjust a position of the distal catheter portion.

6. The catheter assembly of claim 1, further comprising a steering mechanism connected to the proximal catheter portion and configured to adjust a position of the distal catheter portion after insertion.

7. The catheter assembly of claim 1, wherein the catheter assembly includes an inner polyamide layer and an outer polyurethane layer.

8. The catheter assembly of claim 1, wherein the pre-formed bend between the proximal cannula portion and the distal cannula portion is an apex of the angular offset.

9. The catheter assembly of claim 1, wherein the pre-formed curve is a plane curve.

10. The catheter assembly of claim 1, wherein, when the catheter assembly is inserted through the aorta of the patient, the angular offset is configured to bias the distal cannula portion toward the apex of the left ventricle of the patient's heart and away from chordae that actuate a mitral valve of the left ventricle.

* * * * *

UNITED STATES PATENT AND TRADEMARK OFFICE
CERTIFICATE OF CORRECTION

| | |
|---|---|
| PATENT NO. | : 11,986,602 B2 |
| APPLICATION NO. | : 15/168852 |
| DATED | : May 21, 2024 |
| INVENTOR(S) | : Scott C. Corbett et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Eleventh Day of March, 2025

Coke Morgan Stewart
*Acting Director of the United States Patent and Trademark Office*